(12) United States Patent
Guissin et al.

(10) Patent No.: US 8,472,682 B2
(45) Date of Patent: Jun. 25, 2013

(54) MEDICAL IMAGE PROCESSING

(75) Inventors: Avraham Rami Guissin, Moshav Beit-Yanai (IL); Eitan Lavi, Hadera (IL)

(73) Assignee: DVP Technologies Ltd., Tel-Aviv (IL)

( * ) Notice: Subject to any disclaimer, the term of this patent is extended or adjusted under 35 U.S.C. 154(b) by 1170 days.

(21) Appl. No.: 11/991,854

(22) PCT Filed: Sep. 12, 2006

(86) PCT No.: PCT/IB2006/053243
§ 371 (c)(1),
(2), (4) Date: Mar. 12, 2008

(87) PCT Pub. No.: WO2007/031946
PCT Pub. Date: Mar. 22, 2007

(65) Prior Publication Data
US 2010/0158330 A1 Jun. 24, 2010

Related U.S. Application Data

(60) Provisional application No. 60/715,572, filed on Sep. 12, 2005.

(51) Int. Cl.
*G06T 7/60* (2006.01)
*G06T 7/00* (2006.01)

(52) U.S. Cl.
CPC .................... *G06T 7/0012* (2013.01)
USPC ........................................................ 382/128

(58) Field of Classification Search
USPC ................................. 382/128, 261
See application file for complete search history.

(56) References Cited

U.S. PATENT DOCUMENTS

| | | | | |
|---|---|---|---|---|
| 5,050,226 A | * | 9/1991 | Collet-Billon | 382/261 |
| 5,488,670 A | * | 1/1996 | Suzuki et al. | 382/165 |
| 5,523,797 A | * | 6/1996 | Saionji et al. | 348/663 |
| 5,799,111 A | * | 8/1998 | Guissin | 382/254 |
| 6,535,632 B1 | * | 3/2003 | Park et al. | 382/164 |
| 7,428,333 B2 | * | 9/2008 | Asari et al. | 382/167 |
| 7,613,335 B2 | * | 11/2009 | McLennan et al. | 382/128 |
| 2002/0177779 A1 | * | 11/2002 | Adler et al. | 600/476 |
| 2003/0098869 A1 | * | 5/2003 | Arnold et al. | 345/589 |
| 2005/0036668 A1 | | 2/2005 | McLennan et al. | |

FOREIGN PATENT DOCUMENTS
WO WO 2007/031946 3/2007

OTHER PUBLICATIONS

International Preliminary Report on Patentability Dated Feb. 1, 2008 From the International Preliminary Examining Authority Re.: Application No. PCT/IB2006/053243.
International Preliminary Report on Patentability Dated Mar. 27, 2008 From the International Bureau of WIPO Re.: Application No. PCT/IB2006/053243.
Bird "Antenna Feeds", Encyclopedia of Radiofrequency and Macrowave Engineering, p. 185-217, 2005.

(Continued)

*Primary Examiner* — Robert Kim
*Assistant Examiner* — Eliza Osenbaugh-Stewart

(57) ABSTRACT

A method of image processing, including:
(a) calculating at least one pixel color feature (PCF) value for each pixel in a color medical image to generate a set of PCF data; and
(b) filtering the PCF data with at least one spatial adaptive bandpass filter (ABPF) to sort the pixels into physiologically significant regions;
wherein the at least one PCF value for at least one pixel depends on at least 2 color components of the medical image.

52 Claims, 16 Drawing Sheets

OTHER PUBLICATIONS

Evans "Electromagnetic Rewarming: The Effect of CPA Concentration and Radio Source Frequency on Uniformity and Efficiency of Heating", Cryobiology, 40: 126-138, 2000.

Evans et al. "Design of a UHF Applicator for Rewarming of Cryopreserved Biomaterials", IEEE Transactions on Biomedical Engineering, 39(3): 217-225, Mar. 1992.

Foster et al. "Biological Effects of Radiofrequency Energy As Related to Health and Safety", Encyclopedia of Radiofrequency and Macrowave Engineering, p. 511-523, 1999.

Foster et al. "Dielectric Properties of Tissues", Handbook of Biological Effects of Electromagnetic Fields, CRC Press, 2nd Ed.(Chap. 1): 25-101, 1996.

Hambling "Forget Lasers, Phasers and Other Beam Weapons—Radiofrequency Devices Are Here, and They're Set to 'Sting'", Tech Watch: Forecasting Pain, 183(12): 32, Dec. 2006.

Herring et al. "OSU Tunes Into a Cooking Innovation", OSU News & Communication Services, Oregon State University, 2 P., Apr. 30, 2004.

Lapin "N9GL's RF Safety Column: The Military's New RF Waepon", ARRL Handbook for Radio Amateurs, American Radio Relay League, 3 P., 2001.

Liang et al. "Multiband Characteristics of Two Fractal Antennas", Microwave and Oprical Technology Letters, 23(4): 242-245, Nov. 20, 1999.

Penfold et al. "Control of Thermal Runaway and Uniformity of Heating in the Electromagnetic Rewarming of a Cryopreserved Kidney Phantom", Cryobiology, 30: 493-508, 1993.

Repacholi "Radiofrequency Electromagnetic Field Exposure Standards", IEEE Engineering in Medicine and Biology Magazine, p. 18-21, Mar. 1987.

Robinson et al. "Electromagnetic Re-Warming of Cryopreserved Tissues: Effect of Choice of Cryoprotectant and Sample Shape on Uniformity of Heating", Physics in Medicine and Biology, 47: 2311-2325, 2002.

Robinson et al. "Rapid Electromagnetic Warming of Cells and Tissues", IEEE Transactions on Biomedical Engineering, 46(12): 1413-1425, Dec. 1999.

Schwan et al. "RF-Field Interactions With Biological Systems: Electrical Properties and Biophysical Mechanisms", Proceedings of the IEEE, 68(1): 104-113, Jan. 1980.

Scott "Understanding Microwaves", A Wiley-Interscience Publication, 1: 326-331, 1993.

Shelley "Inside View on Deep Heat", Eureka Innovative Engineering Design, 2 P., May 14, 2007.

Von Hippel "Theory: A. Macroscopic Properties of Dielectrics. Comples Permittivity and Permeability", Dielectric Materials and Applications, 1: 3-5, 1995.

Walker et al. "Fractal vol. Antennas", Electronics Letters, 34(16): 1536-1537, Aug. 6, 1998.

Wusteman et al. "Vitrification of Large Tissues With Dielectric Warming: Biological Problems and Some Approaches to Their Solution", Cryobiology, 48: 179-189, 2004.

Hambling "Forget Lasers, Phasers and Other Beam Weapons—Radiofrequency Devices Are Here, and They're Set to 'Stine'", Tech Watch: Forecasting Pain, 183(12): 32, Dec. 2006.

Nischik et al. "Analysis of Skin Erythema Using True-Color Images", IEEE Transactions on Medical Imaging, 16(6): 711-716, 1997.

Office Action Dated Jan. 1, 2012 From the Israel Patent Office Re. Application No. 190102 and Its Translation Into English.

* cited by examiner

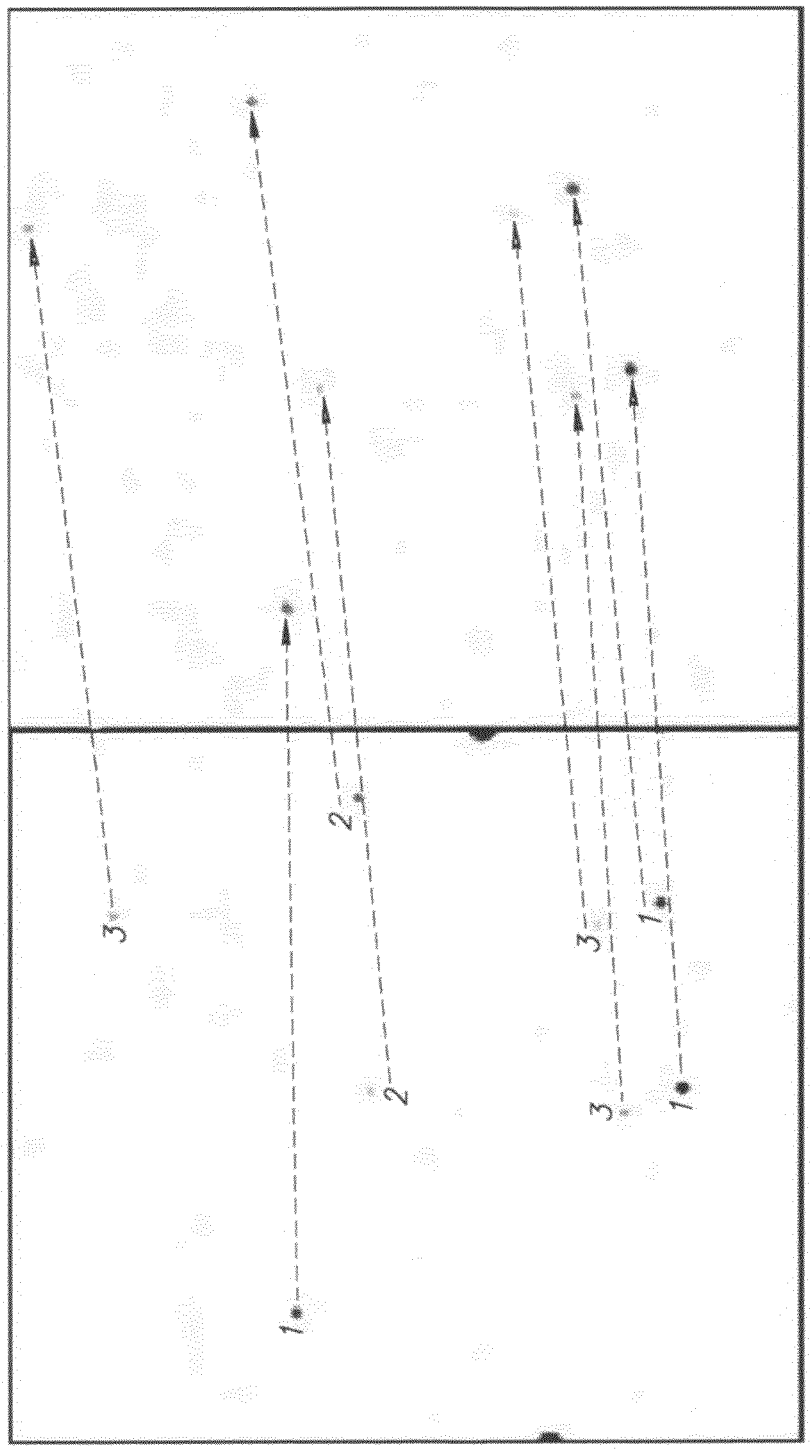

MEDICAL IMAGE PROCESSING

RELATED APPLICATIONS

This Application is a National Phase of PCT Patent application No. PCT/IB2006/053243 having International filing date of Sep. 12, 2006 which claims the benefit under 35 USC 119(e) of U.S Provisional Patent Application No. 60/715,572 filed on Sep. 12, 2005 entitled "BODY PHOTOGRAPHIC IMAGING, REFERENCING AND ANALYSIS FOR MEDICAL AND AESTHETIC APPLICATIONS". The contents of the above Applications are all Incorporated herein by reference.

FIELD OF THE INVENTION

The present invention relates to systems, apparatus and/or methods for image processing, especially medical image processing.

BACKGROUND OF THE INVENTION

In medical procedures it is common for medical personnel to select a sample (e.g. biopsy) based on tissue appearance. For external tissue (e.g. skin) selection may be based upon growth rate, color or other gross anatomic features. For internal tissue (e.g. colon, bladder or stomach) an endoscopic video image may be used to select tissue for biopsy.

Unfortunately, normal tissue and adjacent diseased tissue may often appear similar. In some cases, the tissue of interest may actually be covered by normal mucosa and/or normal tissue. This can make it difficult for medical personnel to select an informative sample based on visual analysis. For this reason, several biopsy samples are typically taken for analysis.

EP patent publication 1 568 307, the disclosure of which is incorporated herein by reference, describes use of luma and/or color features, and linear bandpass spatial filtering, multiple thresholding and logic operations on the multiply thresholded image regions. Image processing described in this application is well suited to detecting small areas with known dimensions in medical images.

US patent publication 2006/0039622, the disclosure of which is incorporated herein by reference, describes image processing methods which rely upon determination of luminance. While the luminance formula includes R, G and B terms, its function is to transform color data into grayscale values. Medical images are not specifically described in the context of the methods.

US patent publication 2005/0171409, the disclosure of which is incorporated herein by reference, describes analysis of "Pixel values" as a means of identifying lung nodules. This application employs a linear discriminant analysis and/or Multi-MTANN. Described methods are suitable for use in analysis of grey values and are not applicable to RGB color data.

US patent publication 2005/0078857, the disclosure of which is incorporated herein by reference, describes an organ searching algorithm for use in medical images and an image coloring algorithm. This application is concerned with converting PGM (grey-map) images to color while identifying organs. Use of RGB data of individual pixels to identify organs is not described as this data is not available from a grey scale map.

U.S. Pat. No. 6,975,898, the disclosure of which is incorporated herein by reference, describes medical image processing for diagnostic purposes. This patent employs directed and scanned optical illumination provided by a scanning optical fiber or light waveguide that is driven by a piezoelectric or other electromechanical actuator included at a distal end of an integrated imaging and diagnostic/therapeutic instrument. This patent teaches that " . . . the white light illumination for standard endoscopic imaging is typically provided through an optical fiber bundle that diffusely illuminates the tissue and is incapable of providing a directed optical energy at high intensity and resolution to produce effective optical therapies, and will often not have the characteristics required for diagnostic processes.".

U.S. Pat. No. 6,208,749, the disclosure of which is incorporated herein by reference, describes a method for computer controlled image analysis of digital skin tissue at a plurality of wavelengths, optionally including those outside of the red-green-blue bands. The described methods and systems can include the automatic characterization of the condition of the skin tissue, based on automatically computed values of parameters which are functions of characteristics of the skin tissue, based on the digital images. Absorbance/reflectance measurements for three spectral bands is apparently suggested as a suitable method for a medical diagnosis. Melanoma diagnosis is specifically considered.

U.S. Pat. No. 6,631,204, the disclosure of which is incorporated herein by reference, describes a similarity measurement method for the classification of medical images into predetermined categories. The described methods employ a small set of pre-classified images and employ a weighted linear combination of eigenvectors for each category. The eigenvectors are equivalent to the Red, Green and Blue base vectors used to describe the entire color space. A test image is provided and projected onto the eigenvectors of each of the categories so as to reconstruct the test image with the eigenvectors. The RMS (root-mean-square) distance between the eigenvectors of the test image and each of the categories is measured. The smallest similarity measurement distance is selected, and the test image is classified in accordance with the selected smallest similarity measurement distance.

U.S. Pat. No. 6,792,137, the disclosure of which is incorporated herein by reference, describes a method for providing a preliminary diagnosis of skin cancer, more specifically a screening risk assessment of pigmented moles and lesions by receiving digital photographs of skin abnormalities from a plurality of consumers at a server, receiving medical information related to each of the plurality of consumers at the server, assigning an identification to at least one of the consumers and the digital photographs, reviewing the digital photographs and categorizing the digital photographs into categories. Use of clinical photographs and/or epiluminescence microscopy (ELM) is described. Color information, if employed, is input manually in text fields.

EP patent 0 588 943, the disclosure of which is incorporated herein by reference, describes use of spatial smoothing operators to smooth images including medical images.

A commercially available HDTV-Compatible Endoscope (EVIS LUCERA; Olympus Industrial; KeyMed (Medical & Industrial Equipment) Ltd, Essex; UK) provides Diagnosis via Mucosal Hemoglobin Value-Responsive Chromatic Enhancement Function, and CV-180 HDTV and NBI processing unit.

U.S. Pat. No. 7,042,488, the disclosure of which is incorporated herein by reference, describes use of color filters for blood vessel color highlighting, including, (R-Y)/(B-Y), where Y is Luma.

U.S. Pat. No. 5,031,036, the disclosure of which is incorporated herein by reference, describes enhancement of endoscopic images acquired with white light, using a color filter, including (G-R).

U.S. Pat. No. 5,956,416, the disclosure of which is incorporated herein by reference, describes the use of three narrow spectral bands to enhance an image based upon an estimate of hemoglobin concentration. When a hemoglobin index IHb which is an indicator of the concentration of hemoglobin in mucosal tissue is calculated as $IHb=32 \cdot Log_2(R/B)$. The IHb color enhancement function works by calculating the average hemoglobin concentration of the tissue, and then displaying those areas with higher-than-average IHb values using more red, and areas with lower-than-average IHb values with more white. Additionally color enhancement is described.

SUMMARY OF THE INVENTION

A broad aspect of some embodiments of the invention relates to image processing which increases visibility of a physiologically important region of a field of view in a medical image. In an exemplary embodiment of the invention, the image is acquired using white light. Optionally, the image can be an internal body image acquired via an intrabody camera, such as using an endoscope, laparoscope, colonoscope, swallowed camera or other means of acquiring an internal image, for example an image of a surface of an intra-body cavity (e.g., GI tract, blood vessels, mouth, airways, sinuses, fluid filled cavities and/or other hollow organs), or an image of an external body surface. In an exemplary embodiment of the invention, increasing visibility is achieved by defining regions which include pixels that represent physiologically similar tissue (e.g. lesions or polyps).

In an exemplary embodiment of the invention, a spectral processing filter is applied to emphasize physiologically significant color data and a spatial filter is applied to reduce noise. In an exemplary embodiment of the invention, the spatial filter is an adaptive bandpass filter (ABPF) which detects regions with unknown dimensions but with similar spectral filter results. In an alternative exemplary embodiment of the invention, a plurality of non-adaptive bandpass filters are used. The results of the filters are optionally combined using a post processing logic. For example, a result of a smaller filter that is within a result of a larger filter, it is considered to indicate a hot spot. If the result is spatially separate, processing can be used to see if it should be identified as a contiguous region or as separate regions.

In an exemplary embodiment of the invention, the spectral processing filter matches the human visual processing system. In an exemplary embodiment of the invention, the spectral filter increases color intensity while maintaining the general colorization of the image.

In an exemplary embodiment of the invention, the spectral processing filter matches spectral properties of physiologically important tissue, for example inflamed, pre-cancerous or cancerous tissue.

Under certain circumstances the use of white light is not considered to be possible by the prior art. In general, white light is not considered to produce images with sufficient sensitivity to small shifts in spectral absorbance to be useful in certain clinical uses, for example assessment of ectopic skin lesions and/or detection of biopsy sites in endoscopic examinations.

The present invention, in some embodiments thereof, demonstrates that it is possible to apply image enhancement algorithms to images acquired using broad band light. Optionally, the broad band light includes a significant portion of the spectrum from which white light is composed, optionally substantially all of the spectrum from which white light is composed. In particular, the broad band optionally includes a significant red component in spite of the fact that red light tends to scatter most (as it has the greatest penetration) and common practice is generally to reduce red components and increase blue components to increase contrast (of intensity, not color). In an exemplary embodiment of the invention, the range of frequencies used is within 0.4-0.8 micron, and optionally comprising a more extensive broad band spectrum in the near infrared of, for example, 0.8-1.1 micron.

Methods according to some embodiments of the invention rely upon shifting of the color balance of absorbance spectra to define regions based upon their content of oxyhemoglobin and/or deoxyhemoglobin, for example a red shift indicating inflammation and a blue shift indicating reduced blood flow and/or extra over layers. Previous attempts to achieve similar results using narrow band light (in particular shorter-wavelength—and penetration—light of about 0.4-0.5 micron) have met with limited success. In an exemplary embodiment of the invention, selection of white light and/or broad band colored light provides both increased luminance and increased parts of a spectra on which changes in color absorption (and reflection) can be identified.

White or broadband light allows for the use of a greater portion of the spectrum of absorption of oxyhemoglobin to determine the areas containing increased amounts of oxyhemoglobin. Unfortunately, use of broadband light, and especially red light, causes substantial diffuse reflectance which, like noise, was believed by the prior art to obviate the benefit of the greater use of spectrum.

In an exemplary embodiment of the invention, the end result of the processing is an image on which are marked a relatively small number of regions of interest. In an exemplary embodiment of the invention, the number of regions marked is smaller than 20, smaller than 10, smaller than 5, smaller than 2. While the number of regions does depend on the actual disease state, in an exemplary embodiment of the invention, the number of regions shown is not more than 3 or 4 times the number of physiologically significant contiguous regions. In an exemplary embodiment of the invention, a region of physiologically significant tissue comprises a set of pixels which correspond to tissue substantially all of which is of physiological relevance, for example, including inflammation, unusual angiogenesis or other lesions of interest. Optionally, the relevance of a region is compared to a similar measurement made at a different time and/or with a different imaging modality, to allow tracking of changes of properties of tissue over time.

In an exemplary embodiment of the invention, such marking includes changing (or overlying) color values on fewer than 30%, fewer than 20%, fewer than 5% or intermediate values of pixels. In color enhancement modes, the percentage of pixels whose colors are changed will generally be higher, for example, 50%, 70% or more.

An aspect of some embodiments of the invention relates to enhancement of physiologically significant regions in a color medical image acquired with broadband light by applying a spectral processing filter which operates on at least two color components of the image in conjunction with a spatial filter. In an exemplary embodiment of the invention, broadband light includes wavelengths characterized by a relatively wide range of penetration depths. For example, the range of penetration depths of different wavelengths in broadband light can be 0.1 mm to 1 mm (generally with short wavelengths going deeper). In an exemplary embodiment of the invention, the spectral processing trades-off image degradation caused by uneven penetration of wavelengths with separation of data from different penetration depths and/or the ability to analyze spectral responses of tissue over a wider range of frequencies. Optionally, the use of broadband or white light allows a more natural image to be presented to a user.

In an exemplary embodiment of the invention, the image is processed using reference values, for example thresholds. Optionally, the reference values are indicative of a physiologic condition. For example, reference values which indicate a high level of oxyhemoglobin can indicate inflammation and/or angiogenesis. Angiogenesis may be indicative of a tumor.

In an exemplary embodiment of the invention, an adaptive bandpass filter (ABPF) is employed to identify a region with unknown size characteristics. Alternatively, a plurality of fixed size filters are used, for example, if target shape can be estimated ahead of time, or even if not.

In an exemplary embodiment of the invention, the results form applying multiple filters, which may be of various types, including both adaptive and non-adaptive, is combined, optionally to improve sensitivity and/or reliability and/or reduce noise. In an exemplary embodiment of the invention, the combining comprises fusing of nearby, and/or overlapping regions. In an exemplary embodiment of the invention, the combining comprises identifying hotspots by being in multiple filter results. In an exemplary embodiment of the invention, reliability is enhanced when a region is highlighted in multiple filters.

An aspect of some embodiments of the present invention relates to combining a spectral processing filter which operates on one, two, three or more color components with an adaptive bandpass filter (ABPF). In an exemplary embodiment of the invention, the three color components are R, G and B as commonly available CCD (or other digital) cameras. In an exemplary embodiment of the invention, the spectral processing filter includes at least one term which indicates a difference between two color components (e.g. R-G). In an exemplary embodiment of the invention, the spectral processing filter emphasizes differences in accordance with human perceptual abilities, at least for some color channels. Optionally, the spectral processing filter includes at least one term which is normalized.

In an exemplary embodiment of the invention, using a larger number of spectral components allows a better discrimination of tissue of interest, for example, tissue with oxygenated hemoglobin. Optionally, the better discrimination is provided by coverage of a larger section of the absorbance spectrum of the tissue of interest.

In an exemplary embodiment of the invention, the use of adaptive spatial filtering allows the reduction of noise even in the presence of unknown shapes of tissue of interest.

In an exemplary embodiment of the invention, the processing modifies only a Luma part but not a Chroma part of the image.

In an exemplary embodiment of the invention, local image contrast is enhanced by maintaining full color balance, while still basing a pixel based gain-factor on separate and independent R, G, B computations.

In an exemplary embodiment of the invention, multiple spatial filters are applied. Optionally, the results of the filters are combined, for example, to increase reliability of result and/or to provide a more complete result.

In an exemplary embodiment of the invention, spectral filtering processing is applied on a result of a spatial filtering.

An aspect of some embodiments of the present invention relates to image processing in which multiple adaptive spatial filters are applied to a medical image, each spatial filter being applied to a different spectrally processed version of the image. In an exemplary embodiment of the invention, the image is acquired using broadband imaging, for example, RGB (e.g., white) light imaging. Optionally, the results of the spatial filters are combined in a manner which reflects an underlying spectral behavior of tissue of interest, for example, oxygenated hemoglobin.

An aspect of some embodiments of the present invention relates to spectral processing of a medical image by comparing multiple spectral filter processing results of a single pixel to reference values. Optionally, the spectral processing filters used match distinctive parts of a frequency spectrum of a tissue of interest.

An aspect of some embodiments of the invention relates to use of spatial adaptive bandpass filters to identify physiologically important regions in a color medical image. Optionally, the image is acquired with white light. Optionally, the filter is applied to numerical data indicative of color.

The term "PCF", as used in this specification and the accompanying claims, refers to an expression which is the result of applying a spectral processing filter to color pixel values.

In general, a PCF is a single numerical value indicative of the three color values Red (R), Green (G), and Blue (B). In an exemplary embodiment of the invention, an Lab image is employed and the term "a" indicates the amount of R or G saturation and the term b indicates the amount of B or Y (yellow) saturation. Optionally, color values may be raised to a power.

Optionally, algorithms according to some embodiments of the invention can be applied to medical images acquired with non white light (e.g. narrow band, IR and/or auto-fluorescent images) and/or images captured using multiple spectral color bands. Optionally, use of these alternative lighting strategies can amplify differences in reflectance characteristics of different tissues within a single field of view. In an exemplary embodiment of the invention, enhancement processing algorithms increase sensitivity of NBI and/or auto fluorescent and/or fluorescent detection.

There is thus provided in accordance with an exemplary embodiment of the invention, a method of image processing, the method comprising:
(a) calculating at least one pixel color feature (PCF) value for each pixel in a color medical image to generate a set of PCF data; and
(b) filtering the PCF data with at least one spatial adaptive bandpass filter (ABPF) to sort the pixels into physiologically significant regions;
wherein the at least one PCF value for at least one pixel depends on at least 2 color components of the medical image.

In an exemplary embodiment of the invention, calculating comprises calculating a color feature which matches a human visual ability. Alternatively or additionally, calculating comprises calculating a color feature which matches a spectra of a tissue absorbance of interest. Alternatively or additionally, practice of the method alters color Saturation and substantially preserves Hue of the image.

In an exemplary embodiment of the invention, filtering comprises modifying a color of at least one pixel.

In an exemplary embodiment of the invention, filtering comprises maintaining the color of substantially all the pixels in the image. Optionally, the method comprises correcting the image after said filtering to maintain a color of said pixels. Alternatively or additionally, the method comprises limiting modification of said image to within saturation of at least one of a representation of said image and a display of said image.

In an exemplary embodiment of the invention, the method comprises separately filtering each color component of said image.

In an exemplary embodiment of the invention, filtering comprises filtering with a plurality of bandpass filters. Optionally, the method comprises combining the results of said filters.

In an exemplary embodiment of the invention, the spatial adaptive bandpass filter defines edges of regions.

In an exemplary embodiment of the invention, filtering comprises thresholding of spatial adaptive bandpass filter results.

In an exemplary embodiment of the invention, the spatial adaptive bandpass filter defines regions without a priori size criteria.

In an exemplary embodiment of the invention, filtering emphasizes at least one region of the image to indicate an amount of oxyhemoglobin.

In an exemplary embodiment of the invention, filtering emphasizes at least one region to indicate an amount of deoxyhemoglobin.

In an exemplary embodiment of the invention, the medical image is an endoscopic image.

In an exemplary embodiment of the invention, the image is acquired using broadband light.

In an exemplary embodiment of the invention, the image is acquired using narrowband light.

In an exemplary embodiment of the invention, the PCF includes at least one term indicating a difference between color components.

In an exemplary embodiment of the invention, the PCF functions as a spectral filter which emphasizes red in the image.

In an exemplary embodiment of the invention, the PCF functions as a spectral filter which emphasizes blue in the image.

In an exemplary embodiment of the invention, the PCF includes a normalization component.

In an exemplary embodiment of the invention, the PCF functions as a spectral filter which evaluates similarity to at least one difference in a hemoglobin absorbance spectra. In an exemplary embodiment of the invention, the PCF functions as a spectral filter which evaluates similarity to at least two differences in a hemoglobin absorbance spectra.

In an exemplary embodiment of the invention, the method comprises repeating (a) and (b) at least two levels of sensitivity.

In an exemplary embodiment of the invention, the method comprises repeating (a) and (b) at least three levels of sensitivity.

In an exemplary embodiment of the invention, the method comprises repeating (a) and (b) at least two types of filtering result, one matched to human vision and one matched to tissue spectra.

In an exemplary embodiment of the invention, the method comprises repeating (a) on a result of (b).

In an exemplary embodiment of the invention, the method comprises applying (a) and (b) as a single combined filter.

There is also provided in accordance with an exemplary embodiment of the invention, a method of image processing, the method comprising:
(a) capturing a medical image using broadband light;
(b) calculating at least one pixel color feature (PCF) value for each pixel in a color medical image to generate a set of PCF data; and
(c) filtering the PCF data with at least one spatial filter to sort the pixels into physiologically significant regions.

In an exemplary embodiment of the invention, said light is white light. Alternatively or additionally, the broadband light includes R, G and B wavelengths. Alternatively or additionally, the white light includes substantially all wavelengths between 460 and 600 nm. Alternatively or additionally, the PCF reflects only two of R, G and B. Alternatively or additionally, practice of the method alters color Saturation and substantially preserves Hue of the image. Alternatively or additionally, the method modifies pixels in accordance with human visual color perception. Alternatively or additionally, the method modifies pixels in accordance with properties of tissue of interest. Alternatively or additionally, the method compares the PCF data to reference values. Optionally, the reference values are derived from a reference spectra. Optionally, the reference spectra includes a hemoglobin absorbance spectra. Optionally, the hemoglobin absorbance spectra includes absorbance spectra of oxyhemoglobin. Alternatively or additionally, the hemoglobin absorbance spectra includes absorbance spectra of deoxyhemoglobin.

In an exemplary embodiment of the invention, the PCF includes at least one term indicating a difference between color components.

In an exemplary embodiment of the invention, the PCF functions as a spectral filter which emphasizes red in the image.

In an exemplary embodiment of the invention, the PCF functions as a spectral filter which emphasizes blue in the image.

In an exemplary embodiment of the invention, said at least one spatial filter comprises a spatial adaptive bandpass filter.

In an exemplary embodiment of the invention, said filter comprises a non-adaptive bandpass filter.

In an exemplary embodiment of the invention, said at least one filter comprises a plurality of filters and wherein filtering comprises combining the results from a plurality of filters.

In an exemplary embodiment of the invention, combining comprises fusing of identified regions.

In an exemplary embodiment of the invention, combining comprises bridging between identified regions.

There is also provided in accordance with an exemplary embodiment of the invention, a method of image processing, the method comprising:
(a) capturing a color medical image using white light; and
(b) calculating at least two pixel color feature (PCF) values for each pixel in the image to generate a first set and a second set of PCF data;
(c) separately applying spatial filters to the first set of PCF data and the second set of PCF data; and
(d) combining the result of the separate applying.

Optionally, the filter comprises an adaptive spatial bandpass filter. Alternatively or additionally, the method comprises sorting pixels based upon conformance to reference values. Optionally, the reference values are prepared by applying one of the two PCFs to a reference spectra. Alternatively or additionally, the reference spectra is an absorbance spectra of a biological material.

In an exemplary embodiment of the invention, the reference values indicate a physiologic condition. Optionally, the physiologic condition is inflammation. Alternatively or additionally, the physiologic condition is a cell proliferation abnormality. There is also provided in accordance with an exemplary embodiment of the invention, a method of image processing, the method comprising:
(a) acquiring an image with white light
(b) applying a first pixel color feature (PCF) to each pixel in the image to generate a first set of PCF data indicative of a first color characteristic;

(c) applying a second pixel color feature (PCF) to each pixel in the image to generate a second set of PCF data indicative of a second color characteristic; and (d) sorting pixels into regions based upon comparison of each of the two sets of PCF data to reference values based upon a reference absorbance spectra.

Optionally, sorting comprises spatially filtering a result of at least one of said (a) and said (b). Alternatively or additionally, at least one of said PCFs is a function of at least two orthogonal color components. Alternatively or additionally, at least one of said PCFs is a function of at least three orthogonal color components. Alternatively or additionally, the sorting defines physiologically important regions. Alternatively or additionally, the reference absorbance spectra is a hemoglobin absorbance spectra.

There is also provided in accordance with an exemplary embodiment of the invention, an apparatus for enhancement of a color medical image, the apparatus comprising:

(a) an input port adapted to receive a color medical image as digital data;

(b) filtration circuitry adapted to apply at least one spectral processing filter to each of a plurality of image pixels to evaluate a color feature of each pixel;

(c) sorting circuitry adapted to define at least one image region by applying an adaptive bandpass spatial filter to the enhanced color features of the pixels. Optionally, said circuitries is adapted to operate in at least two modes, each mode characterized by a successively greater sensitivity. Alternatively or additionally, said circuitries are adapted to operate on images acquired with white light. Alternatively or additionally, the apparatus comprises a marking module adapted to visually delimit the at least one region on the image. Optionally, the marking module adapted to visually alter color Saturation and substantially preserve Hue of the image as it delimits the regions on the image.

BRIEF DESCRIPTION OF THE DRAWINGS

Exemplary non-limiting embodiments of the invention described in the following description, read with reference to the figures attached hereto. In the figures, identical and similar structures, elements or parts thereof that appear in more than one figure are generally labeled with the same or similar references in the figures in which they appear. Dimensions of components and features shown in the figures are chosen primarily for convenience and clarity of presentation and are not necessarily to scale. The attached figures are:

FIGS. 11A and 11B illustrate the possibility of matching identified items in enhanced images acquired at different times from a same subject according to some exemplary embodiments of the invention;

DETAILED DESCRIPTION OF EXEMPLARY EMBODIMENTS

Overview

Figure 1:
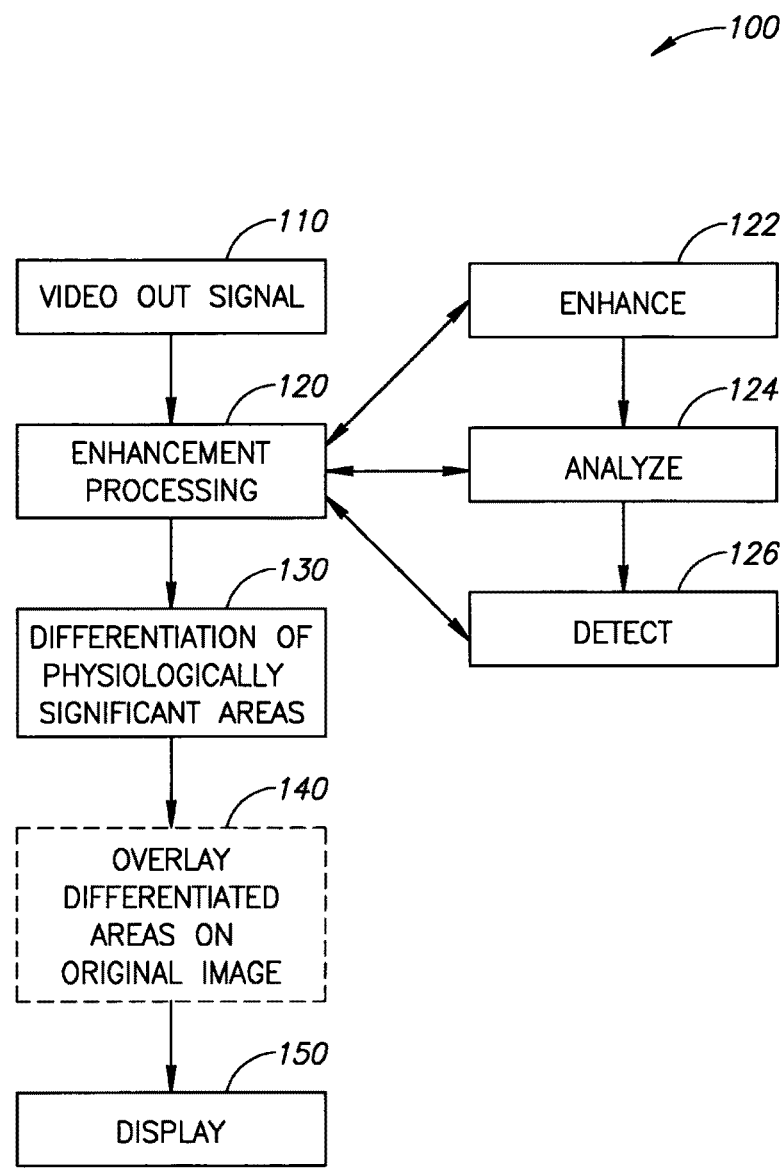
FIG. 1 is a simplified flow diagram illustrating image processing methods according to exemplary embodiments of the invention.

FIG. 1 is a simplified flow diagram 100 of image processing methods according to exemplary embodiments of the invention.

Figure 2:
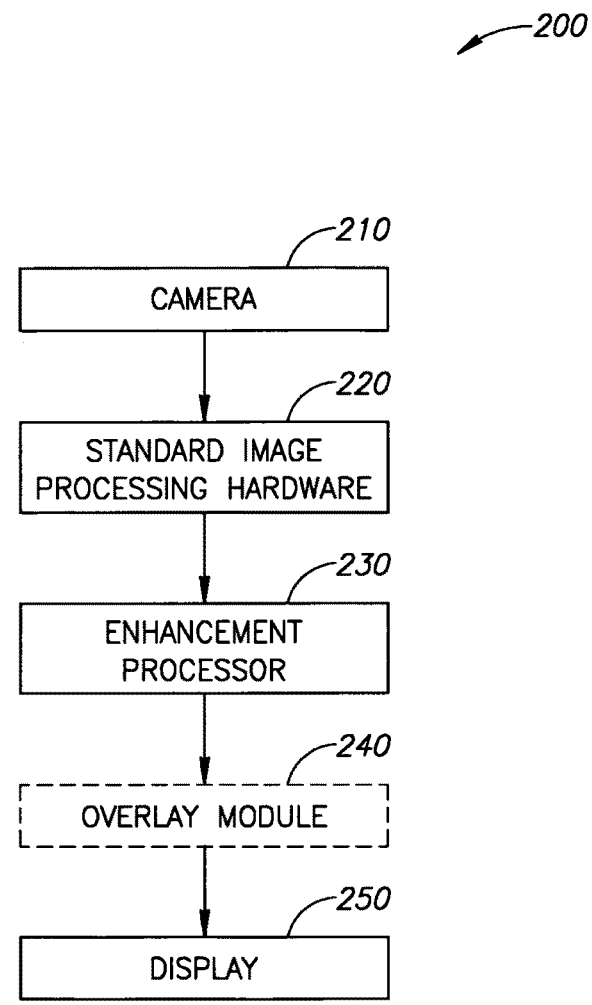
FIG. 2 is a schematic block diagram representation of an image processing system according to exemplary embodiments of the invention.

FIG. 2 is a schematic block diagram representation of an exemplary system 200 according to some embodiments of the invention.

In an exemplary embodiment of the invention, method 100 enhances pixel color by differentiating pixels into groups in a way which increases the ability of a human observer to discern regions when viewing the image, for example, on a computer or video screen. For example, if the threshold color contrast which can be perceived by an observer on screen is 2%, then the invention provides for methods in which the perceived sensitivity is improved ten fold to 0.2-0.5% by mimicking the early stage primate visual processing, combined appropriately with spatial processing, such that for originally weakly discernable changes, a greater contrast is achieved. Alternatively or additionally, other color processing methods are applied, for example as described below.

In order to achieve this natural enhancement, a color image is first represented and modeled, for example, in an RGB broadband representation. This representation preserves (depending on the acquisition method) the spectral distributions employed by red, green and blue cones of the retina. An additional processing stage which employs a color opponency model (e.g., Lab color space which relies on Luma and Chroma components) can then optionally be employed.

In Lab color space, L represents black-white lightness, a is considered indicative of green or red saturation and the b is considered indicative of blue or yellow saturation. In some exemplary embodiments of the invention, a Red-Green opponency (i.e. a of Lab) can be calculated from an RGB image by computing (R-G). Optionally, a Yellow-Blue opponency (i.e. b of Lab) can be estimated by computing a Green-Blue opponency (G-B). Exemplary embodiments of the invention employ one or both of these color opponencies to sort pixels into groups which represent physiologically important regions.

Referring to both FIGS. 1 and 2, method 100 includes enhancement processing 120 of a video output signal 110 from a camera 210 and/or standard image processing hardware 220. Optionally, signal 110 can be stored, for example on a videotape or DVD or CD-ROM disc for subsequent processing. Alternatively or additionally, a single (or series of) digital image from signal 110 can be processed. Optionally, the signal is accessed via a standard signal-out plug or data link. Alternatively or additionally, the methods described herein are integrated into existing image enhancement hardware, rather than provided as a stand alone processor and/or software.

One example of a camera 210 suitable for use in the context of the present invention is the EVIS LUCERA by Olympus described in the background. In an exemplary embodiment of the invention, enhancement processing beyond that achieved by the manufacturer is achieved.

In an exemplary embodiment of the invention, enhancement processing 120 is performed by enhancement processor 230.

In an exemplary embodiment of the invention, enhancement processor 230 employs one or more filters with properties modified to be matched to illumination and/or acquisition spectra of a device used to acquire signal 110.

Optionally, enhancement processor 230 can be provided as a separate hardware unit or incorporated as software or changes in firmware into existing image processing hardware 220.

In an exemplary embodiment of the invention, enhancement processing 120 serves to differentiate 130 physiologically significant areas within a field of view in a medical image.

Figure 6:
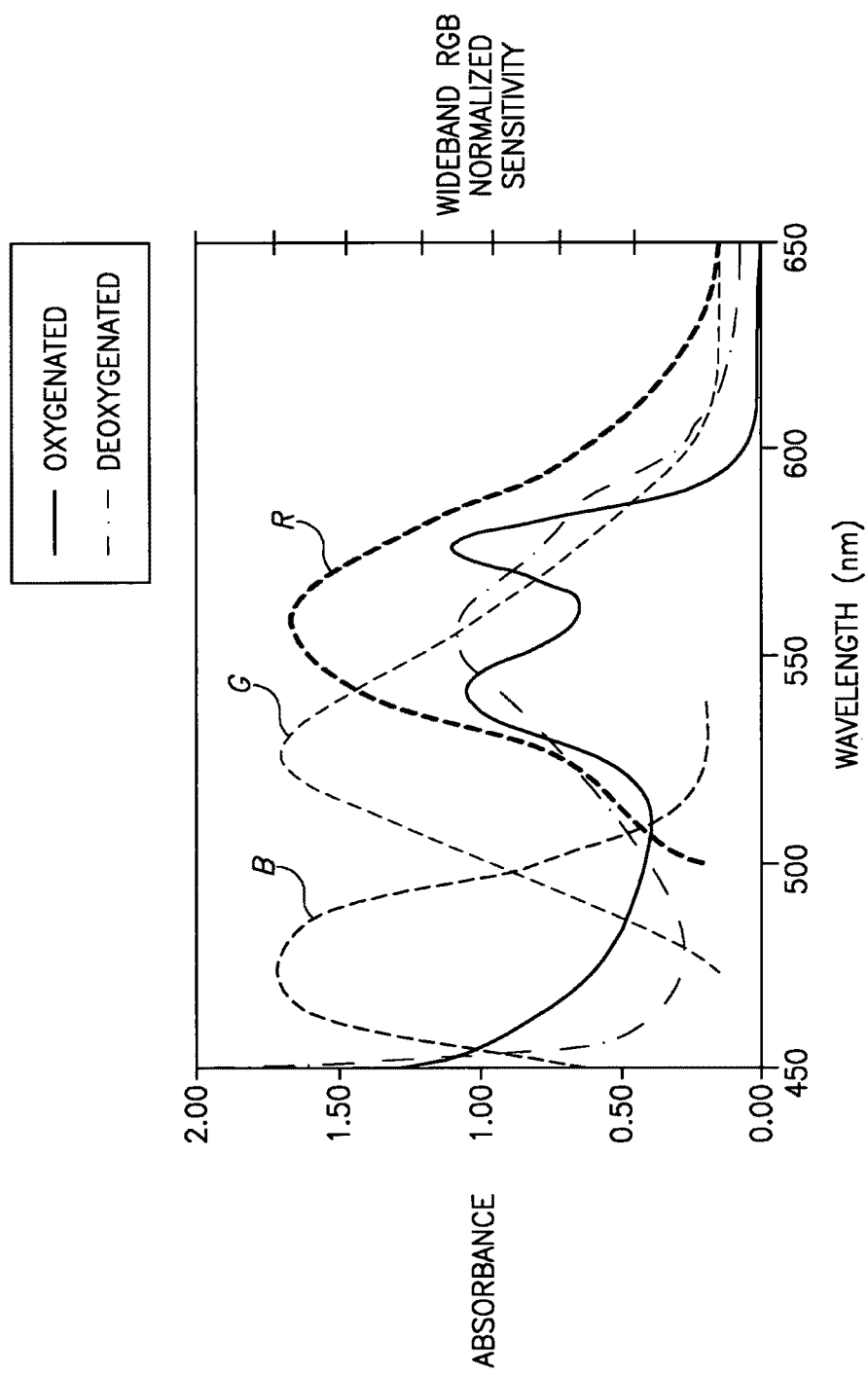
FIG. 6 is a plot of absorbance as a function of wavelength for oxygenated (black line) and deoxygenated (grey line) hemoglobin.

According to an exemplary embodiment of the invention, differentiation 130 relies upon different absorbance/reflectance characteristics of oxyhemoglobin and deoxyhemoglobin as summarized graphically in FIG. 6.

Oxyhemoglobin has absorbance maxima in the red range at about 580 nm and in the green range at about 530 nm.

Deoxyhemoglobin has a single absorbance maximum in the red range at about 560 nm. Moreover, the oxyhemoglobin absorbance in the red range between 600-650 nm is lower than the deoxyhemoglobin, and vice versa in the blue range between 550-450 nm. As a result, the reflectance of oxyhemoglobin and deoxyhemoglobin in response to white light is very different.

In an exemplary embodiment of the invention, small differences in absorbance/reflectance of one or more portions of the spectrum of visible light are amplified to in order to achieve differentiation 130.

Amplification may be achieved, for example, by application of Pixel color features (PCFs) and/or an adaptive spectral bandpass filter and/or two or more spectral bandpass filters.

Once physiologically significant areas within a field of view in a medical image have been differentiated, they can optionally be marked with a uniform color or an outline and overlaid 140 on the image, for example by an optional overlay module 240. Overlay module 240 can be provided as a hardware device or as a firmware or software installation.

After enhancement processing 120 and differentiation 130, an enhanced version of the image, optionally including an overlay, is displayed 150 on display 250 and/or stored in a memory. Optionally, enhancement processing includes spatial filtering. In an exemplary embodiment of the invention, enhancement processing 120 is conducted on an image acquired with broad band light, optionally white light.

In an exemplary embodiment of the invention, medical personnel rely upon the enhanced version of the image, optionally including an overlay, to select one or more sites for biopsy sampling. Optionally, use of method 100 and/or system 200 contributes to a reduction in a number of biopsies used in order to achieve a correct diagnosis. Using currently available graphic image processing technology, it is possible to present the overlay as a translucent area with a color. Optionally, use of a translucent overlay contributes to ease of tracking a biopsy tool as a sample from a selected tissue region (below the overlay) is collected. In an exemplary embodiment of the invention, the enhancement method used preserves the general colorization of the image, so it appears generally natural to the user.

In an exemplary embodiment of the invention, enhancement processing 120 is conducted in one of several modes. Exemplary modes include, but are not limited to, enhance 122, analyze 124 and detect 126. In an exemplary embodiment of the invention, medical personnel use enhance mode 122 to search for physiologically significant areas. Optionally, enhance mode 122 processing is generally designed to improve the low signal to noise ratio of the incoming image signals, while optionally maintaining a natural colorization in the image (e.g., if white light is used).

Once a physiologically significant area has been differentiated 130 in enhance mode 122, camera 210 is optionally steered towards a center of the area. At this point, a still image of the area can be captured and processed 120 in analyze mode 124. Analyze mode 124 applies more sensitive PCFs and/or adaptive spectral bandpass filters and/or non-adaptive spectral bandpass filters to resolve the physiologically significant area into sub-areas with different absorbance/reflectance properties. Analyze mode 124 processing is applied to designated suspected areas in the image, and is optionally characterized by increased sensitivity relative to enhance mode 122, but may produce unwanted noise in portions of the image outside the region identified in enhance mode 122.

If desired, medical personnel and/or system 200 can, activate detection mode 126 on the entire image, or on image regions identified in enhance mode 122.

In an exemplary embodiment of the invention, areas differentiated 130 in one or more of enhance mode 122, analyze mode 124 and detect mode 126 are grouped into one or more regions. In an exemplary embodiment of the invention, these regions are graphically indicated on the image, for example as an overlay or by being colored in a color which contrasts surrounding pixels delineated and overlaid on the image. Optionally, regions defined in 2, or 3, modes are presented concurrently on a single image. Alternatively or additionally, the signal itself is modified, for example, by changing pixel color values therein.

Optionally, medical personnel can return to enhance mode 122 from analyze mode 124 and/or detect mode 126. In an exemplary embodiment of the invention, once a biopsy is taken from a field of view, personnel return to enhance mode 122 and examine one or more additional fields of view.

Alternatively, medical personnel can use analyze mode 124 and/or detect mode 126 to screen entire fields of view. This strategy may be preferred when false positives are more acceptable than true negatives.

Exemplary Underlying Physiologic Considerations

In an exemplary embodiment of the invention, a decrease of the absorbance in the red region of the absorbance spectrum is considered indicative of an increased relative level of oxygenated hemoglobin. This shift to red in the reflectance spectrum color is optionally used to identify physiologically significant processes such as, for example, inflammation and/or a high density of blood vessels. Optionally, the high density of blood vessels indicates angiogenesis.

In an exemplary embodiment of the invention, an increase of the absorbance in the blue region of the absorbance spectrum is considered indicative of a decreased relative level of oxygenated hemoglobin. This shift to blue is optionally used to identify physiologically significant processes and/or tissue types such as, for example, mucosa, polyps, poor circulation and/or tissue necrosis. In an exemplary embodiment of the invention, the necrosis can indicate one or more of gangrene, rapid tumor growth or ischemia.

Optionally, the shifts to red and/or blue occur in cells which are below an imaged surface. In an exemplary embodiment of the invention, use of exemplary enhancement processing 120 detects these shifts and renders them visibly discernible. In an exemplary embodiment of the invention, an ability to detect shifts in reflectance from cells at a given depth below the surface relies upon light wavelengths which penetrate to that depth. Optionally, color processing is used to distinguish contributions from different penetration depths, based on the assumption that a difference between the reflectance in different colors is also dependent on the penetration of that color and not only on the tissue absorbance/reflectance.

In an exemplary embodiment of the invention, ABPFs are employed to define regions with unknown dimensions. Optionally, this ability to define regions with unknown dimensions relies upon measurements of local contrast with regard to one or more PCFs. Optionally, ABPFs can be employed to delimit adjoining regions with high, intermediate or low contrasts with regard to one or more PCFs. In an exemplary embodiment of the invention, ABPFs increase accuracy of border definition and/or increase sensitivity of differentiation between regions. In an exemplary embodiment of the invention, a single ABPF is employed to differentiate regions. Optionally, an ABPF is employed in conjunction with one or more additional filters. Optionally, the additional filters may be either non-adaptive bandpass filters NABPFs or ABPFs.

Optionally, an NABPF is useful in defining adjacent regions characterized by a large relative difference in one or more PCFs. Optionally, a NABPF has a more limited capability to define adjacent regions characterized by a small relative difference in one or more PCFs. In an exemplary embodiment of the invention, differentiation of regions of unknown dimensions and/or regions characterized by a small relative difference in one or more PCFs is achieved by using 2, optionally 4, optionally 8 NABPFs, or intermediate or greater numbers, in combination. In an exemplary embodiment of the invention, a larger number of NABPFs contributes to increased sensitivity. Optionally, the NABPFs are selected so that they cover a range of expected sizes and/or shapes, for example, for round lesions. Optionally, the sizes and/or shapes used depend on the angle of view and/or distance of the lesion, in the image. Optionally, the results of NABPFs are combined to yield a composite result.

In an exemplary embodiment of the invention, an ABPF as described in U.S. Pat. No. 5,799,111 is used, which is multi-directional and recursive. In an exemplary embodiment of the invention, the multi-directionality means that a pixel which is at an edge of a region and when assessed from outside the region may appear less relevant, when assessed from inside the region, appears relevant.

In an exemplary embodiment of the invention, the spatial filters are applied on color filtered results. However, a single filter (e.g., hardware or software) can combine both color and spatial filtering. Such filters may be termed spectral NABPFs or spectral ABPFs.

Acronyms, Symbols and Definitions

In order to facilitate comprehension of the specification, claims and accompanying figures, the following acronyms and symbols are presented and explained as a group.

I=Input image (110); optionally a video stream or still image (e.g., RGB or YCrCb);
   O=Output image;
   R=Red channel of RGB image;
   G=Green channel of RGB image;
   B=Blue channel of RGB image;
   L=Luma component of Lab image;
   a=chroma (red/green) component a of Lab image;
   b=chroma (blue/yellow) component b of Lab image;

"PRP" indicates a pre-processing function applied to I: such as, for example, noise reduction and/or histogram stretching and/or color conversions (e.g. RGB to Lab; YcrCb to RGB; RGB to CYMK or CYMK to Lab or converse conversions);

"PCF" indicates a Pixel Color feature which is a mathematical or logical expression including a term indicative of at least one and (in some embodiments) at least two color values selected from Red (R), Green (G), Yellow (Y) and Blue (B), or other derived color representations such as L, a, b. PCFs are described in greater detail hereinabove in the summary.

"White light" indicates light that includes significant power in substantially all (e.g., at least 70%) frequencies in the visual range. Xenon lamps are a typical example of a white light source. Another example is the mix of colors used for Luma calculation. In some cases, the color balance is somewhat skewed, for example, in daylight colored sources. In an exemplary embodiment of the invention, the percentage of power in each of the red, green and blue bands is about 1/3, optionally the percentage is at least 20% for each band. This last may apply to narrowband light as well (defined below).

"Short-wavelength light" is light that is provided mainly in short wavelengths, such as violet, blue and optionally green. This light typically has a limited penetration (and thus reduced scattering) into tissue.

"Narrowband light" is light which is absent some wavelengths, for example, as described in the following paragraphs. Optionally, narrowband light is provided, in one, two, three, four, five, six or more discrete spectral ranges. Optionally, the frequencies are selected to match tissue absorption characteristics and/or image acquisition characteristics of interest.

"Range Narrowband light" is light whose spectral range is small relative to the visual range of frequencies. For example, the range spanned (from smallest to largest) may be less than 70%, 50%, 30%, 20% or intermediate percentages of the visual range of frequencies. The range may be displaced into the IR or UV spectrum.

"Coverage Narrowband light" is light including components that cover only a part of the visual spectrum, for example, less than 70%, 50%, 30%, 20% or intermediate percentages of the frequency range of the light and/or of the visual range. The coverage may be in several, disjoint frequency ranges and may include components in R, G and/or B bands.

In some cases, illumination may be of various types, but detection is narrowband, etc.

The superscript "E" or "e" generally indicates an exponent.
The superscript "GE" indicates the Green exponent.
The superscript "GRE" indicates the Green Red exponent.
The superscript "BRE" indicates the Blue Red exponent.
The superscript "ae" indicates the a exponent.
The superscript "be" indicates the b exponent.

Tables 1A, 1B and 2 list exemplary subunits useful in constructing PCFs, exemplary PCFs and exemplary PCF+ spatial filter configurations respectively. Table 1b also lists exemplary applications for each PCF.

TABLE 1A

Exemplary PCF Subunits useful in construction of a PCF according to basic processing approaches 1 and 2.

| PCF subunit |
| --- |
| R − G |
| G − B |
| R − B |
| $(G - R)^{GRE}$ |
| $(B - R)^{BRE}$ |
| $G^{GE}$ |
| R/G |
| G/B |
| R/B |
| R/(R + G + B) |
| G/(R + G + B) |
| B/(R + G + B) |
| a |
| b |
| L (Luma of Lab) |
| Hue (H) |

TABLE 1A-continued

Exemplary PCF Subunits useful in construction of a PCF according to basic processing approaches 1 and 2.

| PCF subunit |
| --- |
| Saturation (S) |
| Brightness (B) |
| $a^{ae}$ |
| $b^{be}$ |
| C |
| M |
| Y |
| K |

TABLE 1B

Exemplary PCFs useful in conjunction with exemplary embodiments of basic processing approaches 1 and 2.

| PCF | Exemplary Function |
| --- | --- |
| $G^{GE}*(G - R)^{GRE}*(B - R)^{BRE}$ | Detection of ectopic skin lesions |
| (R − G) − (G − B) | hemoglobin oxygenation |
| (R − G)*(G − B) | hemoglobin oxygenation |
| (R − G)*(R − B) | hemoglobin oxygenation |
| (R − G)/(G − B) | hemoglobin oxygenation |
| (R − G)/(R + G) | hemoglobin oxygenation (normalized) |
| (G − B)/(G + B) | hemoglobin oxygenation (normalized) |
| (R − B)/(R + B) | hemoglobin oxygenation (normalized) |
| (R − G)/(R + G) * (G − B)/(G + B) | hemoglobin oxygenation (normalized) |
| (R − G)/(R + G)/ (G − B)/(G + B) | hemoglobin oxygenation (normalized) |
| (R − G)/(R + G) * (R − B)/(R + B) | hemoglobin oxygenation (normalized) |
| ((R − G) − (G − B))/ (R + G + B) | hemoglobin oxygenation (normalized) |
| a*b | Visual perception enhancement |
| $a^{ae}*b^{be}$ | Visual perception enhancement |
| $SQRT(a^2 + b^2)$ | Visual perception enhancement |
| $(a^{ae} + b^{be})$ | Visual perception enhancement |
| C*M*Y | Visual perception enhancement |
| C*M | Visual perception enhancement |
| C*Y | Visual perception enhancement |
| M*Y | Visual perception enhancement |

TABLE 2

Exemplary PCFs and PCF + Filter combinations according to some embodiments of the invention.

| PCF + Filter combinations[a] |
| --- |
| BPF(R)* BPF(G)* (−BPF(B)) |
| BPF(R*G*(255 − B)) |
| BPF(R − G)*BPF(G − B) |
| BPF((R − G)*(G − B)) |
| BPF((R − G)*(R − B)) |
| $BPF((G - R)^{GRE})$ |
| $BPF((B - R)^{BRE})$ |
| $BPF(G^{GE})$ |
| $BPF(G^{GE}*(G - R)^{GRE}*(B - R)^{BRE}$ |
| $BPF(G^{GE})*BPF((G - R)^{GRE})*BPF((B - R)^{BRE})$ |
| BPF(R/G) |
| BPF(G/B) |
| BPF(R/B) |
| BPF(R/G)* BPF(G/B) |
| BPF(R/(R + G + B)) |
| BPF(G/(R + G + B)) |
| BPF(B/(R + G + B)) |
| BPF(R/(R + G + B))*BPF(G/(R + G + B)) |
| BPF((R/(R + G + B))*(G/(R + G + B))) |
| BPF(a)*BPF(b) |
| $(BPF(a))^{ae} * (BPF(b))^{be}$ |
| $BPF(a^{ae}*b^{be})$ |
| BPF(Hue) |

TABLE 2-continued

Exemplary PCFs and PCF + Filter combinations
according to some embodiments of the invention.
PCF + Filter combinations[a]

BPF(Sat)
BPF(Hue)* BPF(Sat)
BPF((R − G)/(R + G))
BPF((G − B)/(G + B))
BPF((R − B)/(R + B))
BPF((R − G)/(R + G))*BPF((G − B)/(G + B))
BPF(((R − G)/(R + G))*((R − B)/(R + B)))
BPF(C)* BPF(M)* BPF(Y)
BPF(C*M*Y)
BPF(C)*BPF(Y)
BPF(C*Y)
BPF(M)*BPF(Y)
BPF(M*Y)
BPF(C)*BPF(M)
BPF(C*M)

[a]According to various exemplary embodiments of the invention, BPF indicates a bandpass filter which may be adaptive or non-adaptive filter at each occurrence of the term.

The term "F" generally indicates a filtering step. Filtering may be spectral or spatial and adaptive or nonadaptive as indicated in each example hereinbelow.

In an exemplary embodiment of the invention, F can be an Adaptive Band Pass spatial Filter (ABPF). One type of ABPF suited for use in embodiments of the present invention is described in U.S. Pat. No. 5,799,111 the disclosure of which is fully incorporated herein by reference. According to this patent, a difference between two adaptive smooth filters with different smoothing parameters produces an adaptive bandpass filter. ABPFs enable enhancement and detection of image regions without the need to define any expected dimensions of the image regions by defining a required degree of local contrast with respect to adjacent regions. For purposes of this specification and accompanying claims, "adaptive" indicates that special dimensions need not be determined a priori in order to employ the filter.

In an exemplary embodiment of the invention, F can be a Non-adaptive spatial Band Pass Filter (NABPF). NABPFs include, but are not limited to Difference of Gaussians (DOG), or Difference of Boxes (DOB). Optionally, filters of this type can be implemented in one or two dimensions.

Since PCFs may be computed before and/or after filtering F, additional PCF notations are employed as follows:

The term "PCFI" indicates a PCF computed prior to implementation of filter F;

The term "PCFO" indicates a PCF computed after implementation of filter F;

The term "CPCF" indicates a PCF/F combination which optionally includes one or more PCFs and one or more filters F. Functionally, the CPCF is defined by the expression CPCF=(PCFO(F(PCFI(I)))), where PCFI and PCFO may include several different PCFs, and F may include several filters of different types and applied sequentially or in parallel;

The term "H" is used to indicate a statistical histogram of CPCF data. Optionally, H includes one or more of average, standard deviation and upper and/or lower percentile levels;

The term "T" is used to indicate a threshold which employs percentile levels computed in "H" to define boundary edges of a region;

The term "L" is used to indicate a logical analysis of the results of application of T to H.

In an exemplary embodiment of the invention, combination of T output from multiple CPCFs improves the reliability of differentiated regions.

In an exemplary embodiment of the invention, combination of T output from multiple CPCFs improves the sensitivity of differentiation between regions.

In an exemplary embodiment of the invention, combination of T output from multiple CPCFs provides a geometrical and/or morphological relationship between small and large differentiated regions. Optionally, the small regions may be within and/or overlapping and/or in proximity to the larger regions. In an exemplary embodiment of the invention, the small regions indicate "hot spots" of especial interest within a larger region that is generally of interest.

The term "S" is used to indicate a segmentation analysis of the results of application of L to T. Optionally, S includes blob analysis of differentiated segments with respect to one or more of area, strength and bounding dimensions and/or labeling the segments and/or extracting boundaries. Optionally, the order in which S and L are applied may be reversed.

The term "D" is used to indicate display processing of an output 0 of preceding steps. In an exemplary embodiment of the invention, D includes overlay of differentiated areas and/or their boundaries and/or features (e.g. scores, labels) onto input image I, or enhanced image indicated by the term E.

The term "E", when not employed as a superscript, is used to indicate enhancement of the image. In an exemplary embodiment of the invention, E includes combination of CPCFs resulting from one or more of PCFI, F, PCF and H to improve display and/or visual differentiation of the image.

Optionally, E relies upon dynamic range compression (DRC) of one or more components of the CPCFs using a lookup table (LUT) based upon local or global histogram analysis (DRCLUT).

Optionally, E relies upon dynamic range stretching (DRS) of one or more components of the CPCFs using a lookup table (LUT) based upon pre-computed stretching, (e.g. expanding, gain) functions or local or global histogram analysis, or both (DRSLUT).

The term "B" is used to indicate image buffering providing graphical overlay for the display of investigation and detection data (visual, alphanumeric and graphic). In an exemplary embodiment of the invention, borderlines of suspected regions are superimposed onto the enhanced image via graphical overlay. Optionally, this enables an observer to more easily discern a perimeter of a potential biopsy collection region. Optionally, colors of the borderlines are selected to indicate a clinical significance and/or as in consideration of colors in the background image. Optionally, consideration of colors in the background image contributes to visualization. Optionally, such overlays are selectably displayed or hidden, for example, using a manual control such as a switch or button (hand or foot) or using a graphical user interface, such as a mouse, keyboard and/or screen interface.

The term "POP" is used to indicate a Post Processor function. In an exemplary embodiment of the invention, POP provides color back conversion to the appropriate image representation for display as a function of the display monitor.

Exemplary Image Processing Approach 1: Discriminant Function

Figure 3:
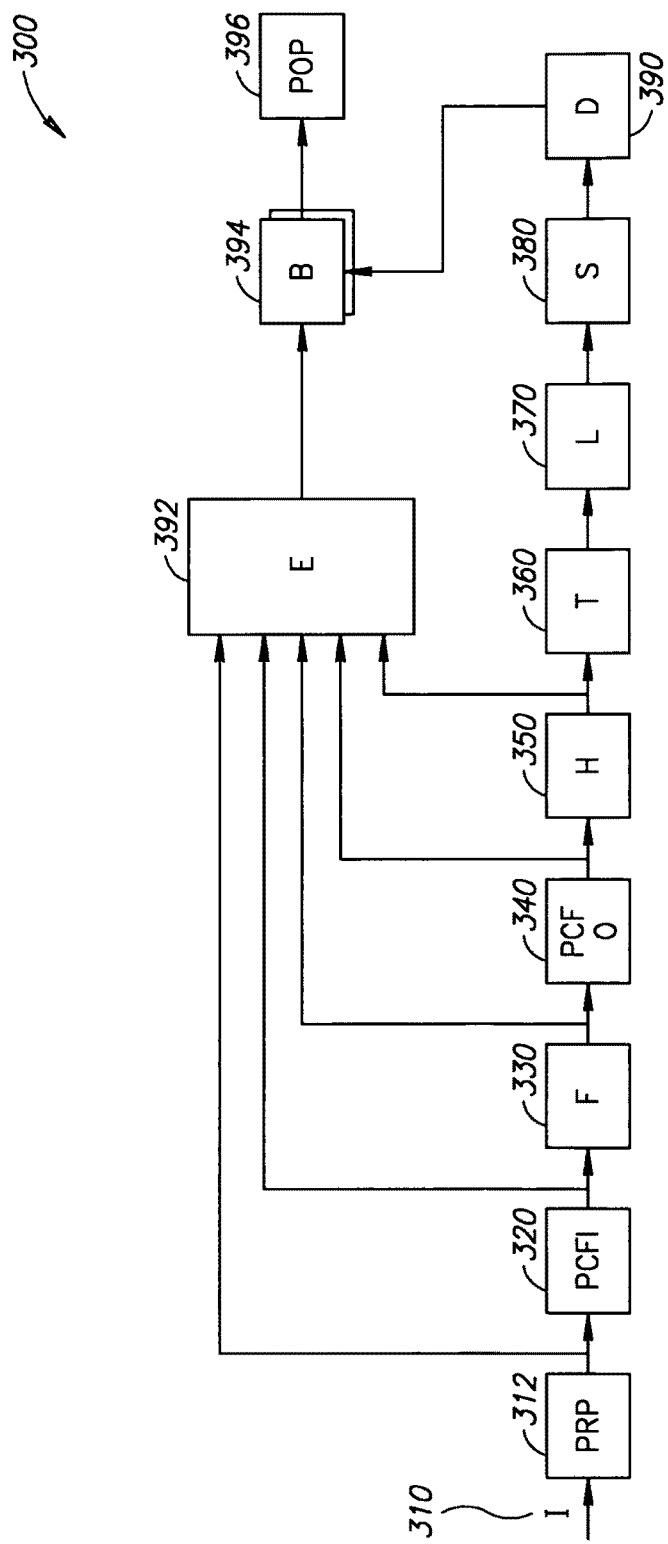
FIG. 3 is a flow diagram illustrating in more detail the enhancement processing of FIG. 1 according to some embodiments of the invention.

FIG. 3 is a schematic block diagram of an exemplary image processing approach 300 which shows in greater detail some embodiments of enhancement processing 120 of FIG. 1. In the exemplary approaches shown, not all the acts must be carried out as described and some may be omitted, changed and/or changed in order.

In an exemplary embodiment of the invention, approach 300 modifies displayed pixel values (or provides an overlay) using spectral processing. Optionally, one or both of two different types of spectral filters are applied, a filter used for enhancing the image and a filter used for emphasizing certain tissue in the image.

Optionally, the following equation is used:

$$O=POP(D(E,S(L(T(H(PCFO(F(PCFI(PRP(I))))))))))$$

An enhancing filter, used, for example, during regular viewing, serves to enhance a digital image in a manner compatible with the human visual system. In an exemplary embodiment of the invention, filtering numerical values representing pixel color with a spatial filter enhances natural colors and/or color differences. In an exemplary embodiment of the invention, processing 120 produces an image which retains the natural color scheme while making the different regions more distinct from one another. Optionally, color Saturation is altered while original image Hue is substantially preserved.

An emphasizing filter, used, for example, during image analysis, is selected to match spectral properties of tissue of interested, for example, inflamed tissue or cancerous or precancerous tissue. In an exemplary embodiment of the invention, this emphasizing filter is selected based on a matching of peaks and valleys (and relative peak amplitudes) of the spectra of interest, as compared to the spectra of the image acquisition means and/or illumination means. This may result in an image with distorted colorization. Optionally, the results are thresholded and/or shown as an overlay.

At 310 input I, typically a digital video stream, but optionally a single digital image is provided.

At 312, input I is subject to preprocessing PRP as described hereinabove in definitions to produce PCFI 320.

In one specific exemplary embodiment of the invention, three PCFIs are produced:

PCFI(1)=L of I
PCFI(2)=a of I
PCFI(3)=b of I

In an exemplary embodiment of the invention, approach 1 is applied initially in enhancement mode 122. According to some embodiments of enhancement mode 122, PCFI(1), PCFI(2) and PCFI(3) are each subject to enhancement processing E at 392. This process produces:

E(1)=Enhanced output of Luma component
E(2)=Enhanced output of color component a
E(3)=Enhanced output of color component b In an exemplary embodiment of the invention, E relies upon a sum of DRCLUT and DRSLUT as defined hereinabove so that E(1), E(2) and E(3) represent:

$$E(1)=DRCLUT1(PCFI(1))+DRSLUT1(F(PCFI(1)));$$

$$E(2)=DRSLUT2(PCFI(2))+DRSLUT3(F(PCFI(2)));$$

$$E(3)=DRSLUT4(PCFI(3))+DRSLUT5(F(PCFI(3)));$$

where

DRCLUT1 and DRSLUT1 to DRSLUT5 are lookup tables computed separately on the basis of the histograms of each of PCFIs 1 through 3. In order to maintain color hues in the enhanced imagery it is possible to set DRSLUT2=DRSLUT4 and/or DRSLUT3=DRSLUT5.

Optionally, color representation is preserved, while taking into account an imperfect orthogonality between L, a and b, for example, due to the effects of saturation.

In an exemplary embodiment of the invention, the RGB components are amplified equally, thereby maintaining their respective ratios while enhancing their relative Luma contrasts. For example, if only the first expression E(1) is used for the enhanced output of the Luma component, then the per pixel Luma gain factor is given by the ratio of the Luma output E(1) divided by the input Luma PCFI(1). This gain ratio G1=(E(1)/PCFI(1)) is then applied to all R, G, B color components and maintains the color balance per pixel while still enhancing the image. Optionally, the gain ratio is limited such that E(1) is remains within the dynamic range of the signal and display representation (e.g. no saturation or cut off).

In an alternative embodiment of the invention, the filter F (e.g. ABPF, NABPF) is applied to all three color components R, G, B, and the maximum gain factor per pixel of the three components is determined such that the enhanced result of all color components remains within the dynamic range of the signal and/or display representation (e.g. no saturation or cut off), while also retaining the color balance.

According to some embodiments of enhancement mode 122, PCFI(1), PCFI(2) and PCFI(3) are each subject to filtering F at 330.

Optionally, F can include an ABPF and/or a NABPF as described hereinabove in the definitions.

In an exemplary embodiment of the invention, an ABPF is employed at F. Exemplary ABPFs include, but are not limited to:

$$ABPF=ASF1-ASF2$$

$$ABPF=(ASF1-ASF2(ASF1))$$

where ASF1 is an adaptive smoothing filter using fine smoothing parameter and ASF2 is adaptive smoothing filter using coarse smoothing parameter. Optionally, ASF1 and/or ASF2 is a multi-dimensional multi-directional adaptive spatial filter as disclosed in U.S. Pat. No. 5,799,111.

In an exemplary embodiment of the invention, a NABPF is employed at F. Exemplary NABPFs include, but are not limited to:

$$NABPF=NASF1-NASF2$$

$$NABPF=(NASF1-NASF2(NASF1))$$

where NASF1 is 1 non adaptive smoothing filter (e.g. Gaussian or box) using fine smoothing parameter and NASF2 is a non adaptive smoothing filter (e.g. Gaussian or box) using coarse smoothing parameter, resulting in Difference of Gaussians (DOG), or Difference of Boxes (DOB).

In an exemplary embodiment of the invention, approach 1 is applied in analyze mode 124 and/or detection mode 126. Optionally, PCFIs and/or filters F in these modes are as described above for enhance mode 122. Alternatively, other PCFIs and/or filters F are employed, for example those listed in table 1 above.

At 340, the result of filter F is expressed as PCFO:

$$PCFO1=(F(PCFI2))*(F(PCFI3)).$$

At 350 a histogram analysis H is applied to each PCFO as described above in definitions.

At 360, one or more thresholds T are applied to each PCFO. In an exemplary embodiment of the invention, two different thresholds T are applied to PCFO1 concurrently.

At 370, the following logic L is used to divide the image into four separate segmenting maps S (370) as follows:

If (PCFI (2)>0 & PCFI (3)>0) $S_{++}=(T_{++}(PCFO1)$
If (PCFI (2)>0 & PCFI (3)<0) $S_{+-}=(T_{+-}(PCFO1)$
If (PCFI (2)<0 & PCFI (3)>0) $S_{-+}=(T_{-+}(PCFO1)$
If (PCFI (2)<0 & PCFI (3)<0) $S_{--}=(T_{--}(PCFO1)$

In an exemplary embodiment of the invention, maps S are overlaid on displayed image 390 and/or stored in buffer 394 and/or sent to POP 396.

In an exemplary embodiment of the invention, method 300 employs standard "white" light. This permits practice of method 300 during a standard medical procedure (e.g. endoscopy and/or laproscopy or other imaging via tubes, such as colonsocopy) and reduces a need for expensive light sources (e.g. narrow band, IR and/or fluorescent excitation).

In an exemplary embodiment of the invention, method 300 employs standard narrow band imaging wavelengths and/or florescent excitation wavelengths. While these lighting schemes are generally known in the art, application of image enhancement processing algorithms to images produced using these lighting schemes is not generally performed. Those of ordinary skill in the art generally consider it more expedient to adjust lighting parameters to achieve a best image when working with narrow band imaging wavelengths and/or florescent excitation wavelengths.

Figure 4:
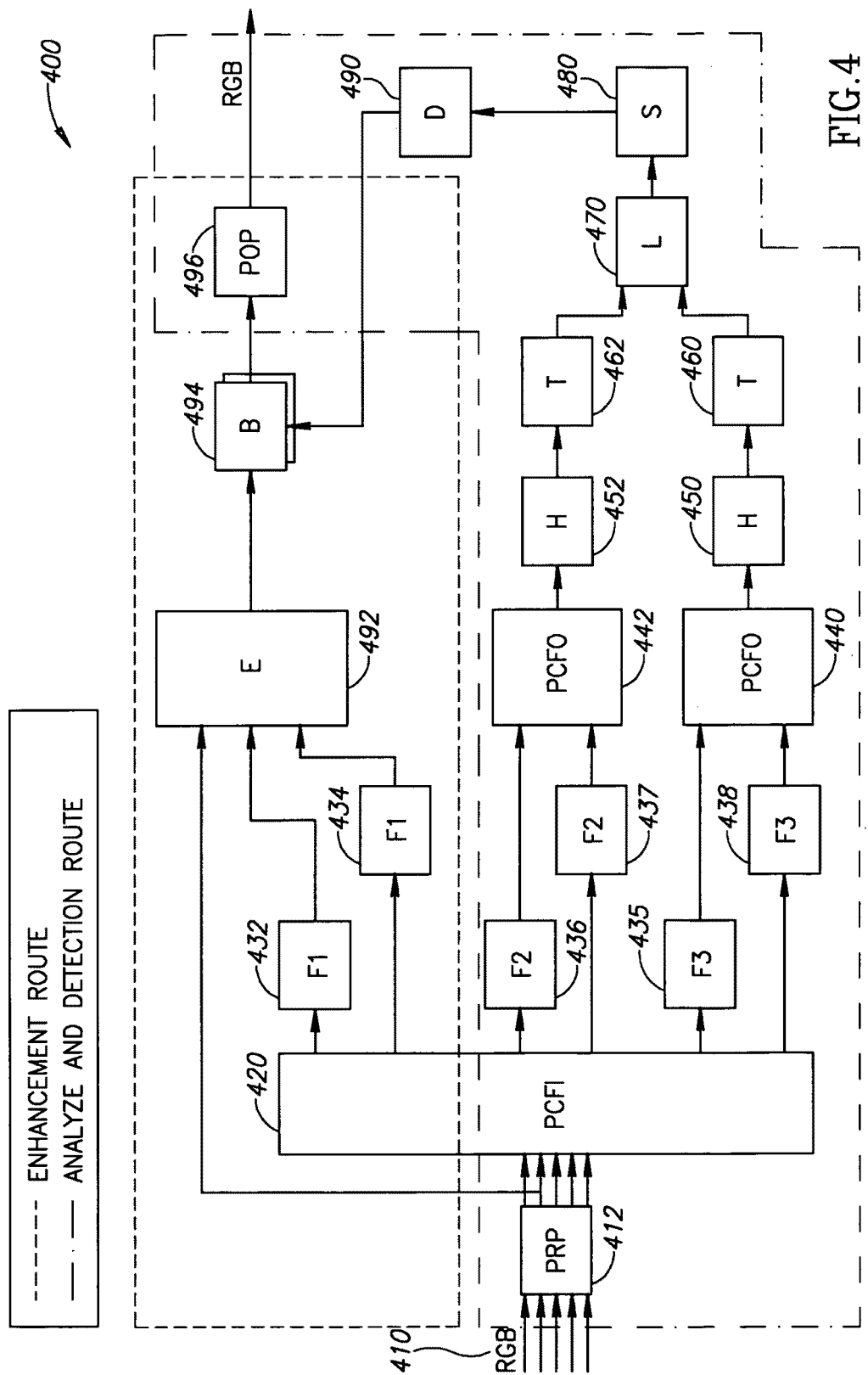
FIG. 4 is a more detailed flow diagram of the enhancement processing of FIG. 3 including operation in multiple modes according to some embodiments of the invention.

FIG. 4 illustrates an additional exemplary enhancement processing method 400, similar to method 300, in greater detail. The depicted embodiment illustrates an exemplary filtering architecture whereby enhance and detect routes are provided as a function of the respective processing functions. Input RGB signal 410 corresponds to I 310. Items 412, 420, 470, 480, 490 492, 494 and 496 correspond to items 312, 320, 370, 380, 390, 392, 394 and 396 in FIG. 3 as explained above.

In FIG. 4, an exemplary image enhancement 122 sequence is indicated by short dotted lines (upper portion of figure), and analysis (124) and/or detection (126) is indicated by longer dashed lines (lower portion of figure).

In the depicted embodiment, enhancement 122 includes application of one or more filters 432 and 434.

In the depicted embodiment, analysis (124) and/or detection (126) include parallel paths.

An exemplary first path includes filters 436 and 437, PCFO 442, histogram 452 and threshold 462.

An exemplary second path includes filters 435 and 438, PCFO 440, histogram 450 and threshold 460.

Optionally, the paths merge at L 370.

Exemplary Image Processing Approach 2: Spectral Distribution

Figure 5:
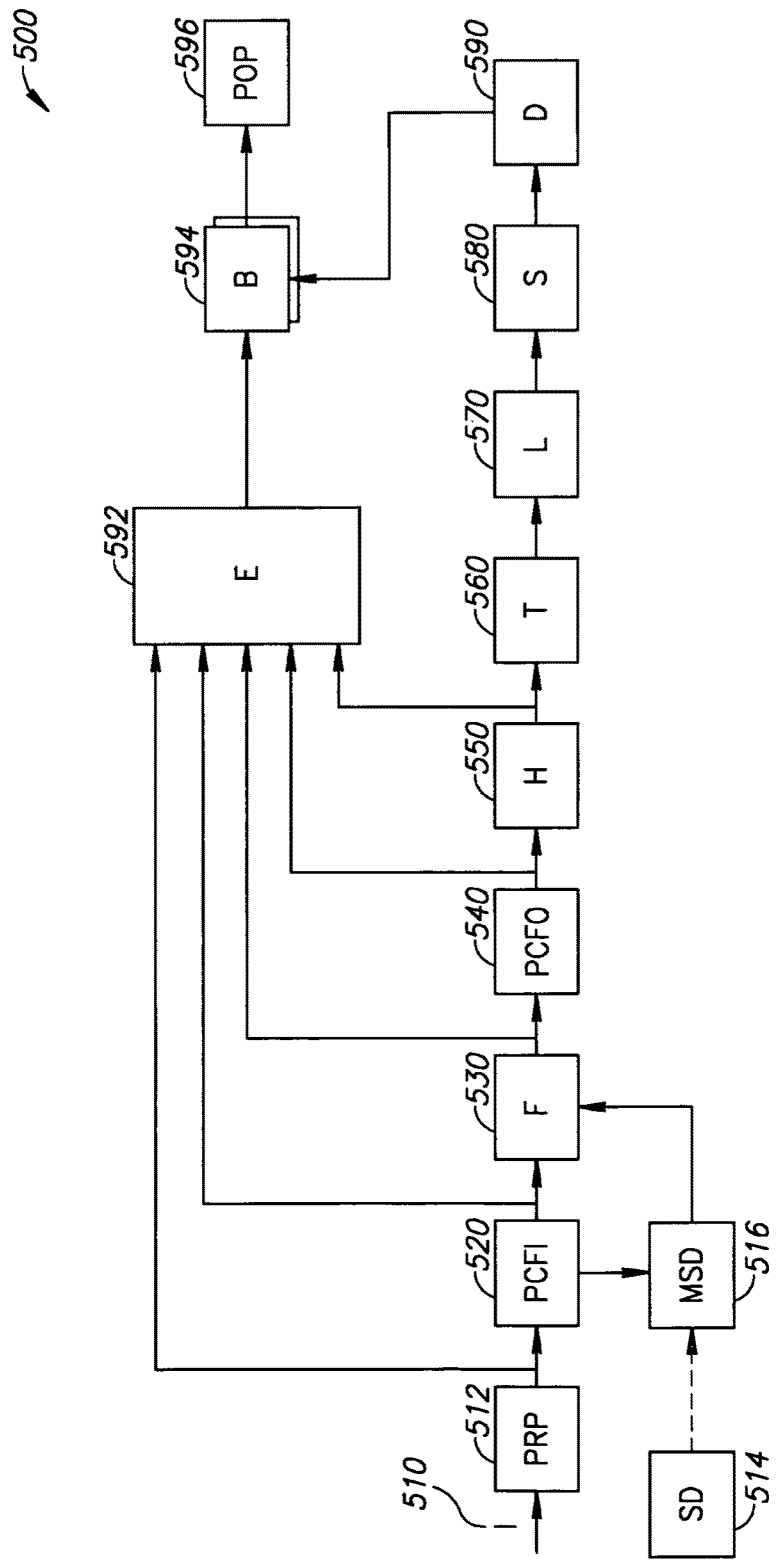
FIG. 5 is a flow diagram illustrating in more detail the enhancement processing of FIG. 1 according to some additional embodiments of the invention.

FIG. 5 is a schematic block diagram of an additional exemplary image processing approach 500 which shows in greater detail some other embodiments of enhancement processing 120 of FIG. 1. Items 510; 512; 520; 530; 540; 550; 560; 570; 580; 590; 592; 594; and 596 correspond to items identified with similar letters in FIG. 3.

In the spectral distribution approach, each pixel in the image is compared to a reference value, instead of, or in addition to, being compared relative to other pixels in the image.

Methods according to approach 500 can be used to detect specific substrates mixed with other materials. In an exemplary embodiment of the invention, hemoglobin concentration in cells is analyzed.

At 514 spectral distributions (SD) of one or more reference spectra (e.g. oxyhemoglobin and deoxyhemoglobin) are collected as pre-computed reference data. In an exemplary embodiment of the invention, one or more reference statistics (e.g. R-G and/or R-B) are derived from the reference spectra at different wavelengths.

In an exemplary embodiment of the invention, multiple PCFs, in the form of relative correlations to reference statistics, are used to identify various physiologically distinct tissue types. For each color component, SDs are assigned to one of two, optionally three, optionally four or more quanta categories (e.g. low and high or low, medium and high).

For example, in an RGB color image with three possible distinct reflectances (low, medium and high) per color, there are 27 ($3^3$) possible combinations of R, G and B values for each pixel. Optionally, normalization of R, G and B values to percent of total reflectance (for example, r=R/(R+G+B), g=G/(R+G+B), b=1−r−g), reduces the number of combinations to 10. At 516, MSD PCFIs are optionally matched to reference PCF SDs on a pixel by pixel basis and image distance maps to best match per pixel are generated. Preparation of distance maps optionally relies upon calculation of a correlation as $C_p$ as summarized in the equation below $$C_{p,i} = \frac{\left(\sum_{j=1\ldots n} p_{j,r} \cdot p_{j,i}\right)}{\left(\sum_{j=1\ldots n} p_{j,r}^2\right)^{1/2} \cdot \left(\sum_{j=1\ldots n} p_{j,i}^2\right)^{1/2}}$$

Where, p indicates the particular PCF used;
r indicates reference value for p;
i indicates image pixel location;
j indicates the respective PCF indexed components; and
n indicates the number of PCFs used per pixel.

In an exemplary embodiment of the invention, n=3 with PCFs $p_1$=r, $p_2$=g, $p_3$=b where r, g, b are normalized R, G, B color components as described above. In another exemplary embodiment of the invention, n=2 with PCFs $p_1$=(r−g), $p_2$=(b−g) where r, g, b are normalized R, G, B color components as described above. In an exemplary embodiment of the invention, this embodiment is used to match to two peaks and one valley in the hemoglobin spectra.

In an exemplary embodiment of the invention, calculation of $C_p$ permits an evaluation of how well a particular pixel conforms to reference statistics r. A large $C_p$ suggests that the pixel is influenced to a large extent by the material that provided the reference spectrum from which the reference statistics were derived. A small $C_p$ suggests that the pixel is influenced to a small extent by the material that provided the reference spectrum from which the reference statistics were derived.

As in the discriminant approach described above, MSD $C_p$ results may be subsequently filtered by multiple ABPFs and/or NABPFs, followed by PCFOs, histogramic analysis and thresholding, and sorting into regions based upon their $C_p$ value, for example by use of one or more thresholds T.

Imaging External Surfaces of the Body

In an exemplary embodiment of the invention, external body surfaces are imaged and enhanced. Imaging can be of the whole body or selected portions of the body. Optionally, the images include geometrical references. These references can serve to align photographs of a same body portion taken at different times and/or to align photographs of different body portions to assemble a composite image of a larger area.

According to some embodiments of the invention input image I is an image of skin and enhancement processing 120 functions as a computer assisted screening method which provides skin abnormality detection and/or analysis. Optionally, skin lesions can be tracked over time to assist medical personnel in assessing clinical progression of abnormalities. In an exemplary embodiment of the invention, medical personnel employ analyze mode 124 and/or detection mode 126 and/or ex-vivo analytic procedures conducted on biopsy samples to make a diagnosis.

According to some exemplary embodiments of the invention, camera 210 includes more than one camera. An exemplary multi camera configuration is shown in FIG. 7.

Figure 7:
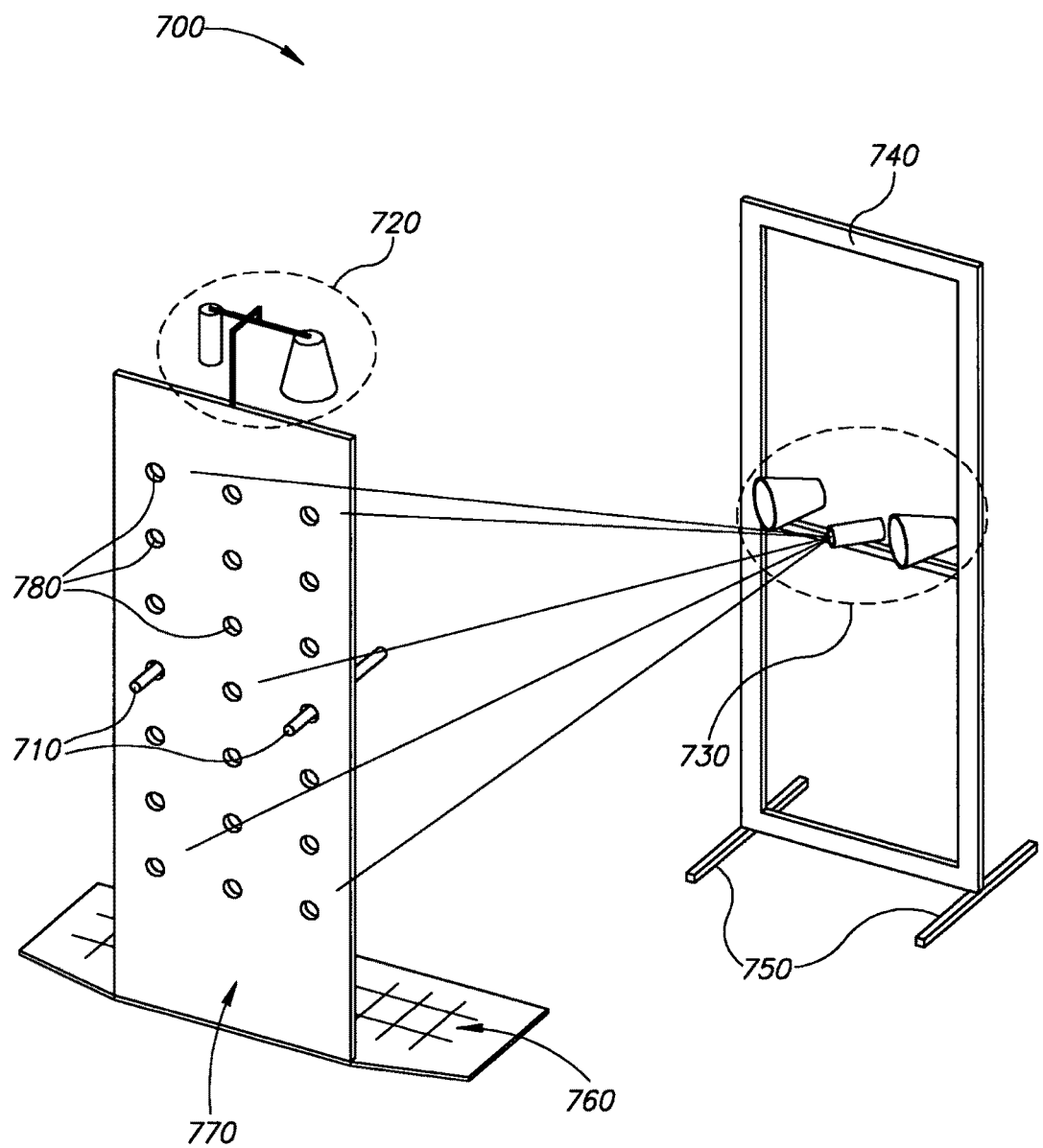
FIG. 7 is a perspective view of a camera module suitable for use in some embodiments of a system as diagrammed in FIG. 2.

FIG. 7 depicts a camera module 700 including a laterally displaced camera unit 730 and a vertically displaced camera unit 720. Module 700 also optionally includes a subject posing stand 770. Posing stand 770 can include, for example, two or more body part supports 710 which can be positioned as desired in support engagement receptacles 780 in posing stand 770. Posing stand 770 optionally includes one or more positioning grids 760. In an exemplary embodiment of the invention, use of supports 710, receptacles 780 and/or grids 760 permits positioning of a subject in a position which exposes a desired skin are to one or more of camera units 720 and/or 730. Optionally, the subject is supported and/or positioned in such a way that they do not move during a period of time sufficient for acquisition of several images. Optionally, the several images are overlapping images and/or images captured using different photographic conditions (e.g. lighting; F stop and/or shutter speed).

Optionally, a same subject is similarly positioned with respect to posing stand 770 using supports 710, receptacles 780 and/or grids 760 during two photography sessions conducted at different times. In an exemplary embodiment of the invention, this similar positioning permits direct comparison of images acquired during the two sessions. Optionally, this contributes to accurate clinical follow up of specific lesions and/or general progression of a clinical condition (e.g. number and/or density of lesions).

In an exemplary embodiment of the invention, each of camera units 730 and/or 720 includes a high resolution, color digital camera equipped with an optical lens with optional zoom capabilities, appropriate light sources, a stand (e.g. 740 with a base 750 or 770) which enables manual or computer controlled motorized vertical and horizontal translation of the camera and light sources, which enables the translational direction of the camera line of sight to the various body parts. Optionally one or more of camera units 720 and 730 incorporates a color still or video camera with a near infrared (NIR) capability, whereby the light sources include diffusive light as well as a narrow spectral band directed NIR light, all of which are preferably located in the vicinity of the camera and are translated together with the camera.

In an exemplary embodiment of the invention, the NIR directed light source is placed in proximity to or along an optical axis of a camera. Optionally, the NIR directed light source uses a same divergence as the optical field of view of the camera. In this way, the NIR source can cover the photographed field of view with direct NIR illumination. Optionally, the NIR light source can employ one or more of a laser, a diode laser, or another diode technology with appropriate diverging optics. Optionally, the directed, narrow band NIR light is employed for detection of retro reflective fiducials which are optionally placed on the photographed subject. The fiducials provide reference information in the image (e.g. for assembly of multiple images and/or comparison of temporally disparate images). In an exemplary embodiment of the invention, the combination NIR/color camera is fitted with a spectrally matched narrow band filter. The filter optionally rejects broad spectrum diffuse light.

Optionally, camera units 720 and/or 730 are equipped with a camera pan and tilt mechanism. In an exemplary embodiment of the invention, the pan/tilt mechanism enables angular coverage of all body parts. This process optionally simplifies and/or accelerates image capture relative to conventional step-stare procedures.

In another exemplary embodiment of the invention camera units 720 and/or 730 are initially operated in enhance mode 122 at a first (relatively low) resolution. Optionally, once a region of interest is defined, camera units 720 and/or 730 are aimed at the region of interest and camera optics are zoomed in to provide a higher resolution image which can be enhanced 120 in analyze mode 124 and/or detect mode 126.

Optionally, additional screening in enhance mode is subsequently conducted to identify additional regions of interest.

In another exemplary embodiment of the invention, a single camera unit (e.g. 730) includes two or more separate cameras. Optionally, each separate camera is characterized by a width of a field of view.

In an exemplary embodiment of the invention, one camera employs a wide field and serves for identification of regions of interest in enhance mode 122.

In an exemplary embodiment of the invention, one camera employs a narrow field of view. Optionally, this camera can be focused on regions of interest and operated at a higher resolution in analyze mode 124 and/or detect mode 126. In an exemplary embodiment of the invention, high resolution images of suspected lesions are stored (e.g. as thumbnail images) for future analysis and comparison for clinical follow-up of specific lesions.

In an exemplary embodiment of the invention, a camera unit (e.g. 730 includes two or more cameras (optionally identical) with overlapping fields of view. The overlapping fields of view can provide independent lesion detection and/or facilitate triangulation for computing distances (e.g. to and/or between one or more detected lesions). The paired cameras can also provide multiple observation angles with respect to a single lesion. Optionally, the multiple observation angles increase a probability of detection and/or contribute to an ability to reduce interference from obstructions (e.g. body hair). Alternatively or additionally, multiple observation angles can be achieved by rotating the subject.

Optionally, posing stand 770 is uniform in color (e.g. blue). Optionally, the same color is used in a vertical portion and a floor mat of stand 770. Optionally, the vertical portion and/or the floor mat include indexed reference grids 760 and/or a color reference tablet for color calibration, and/or mechanically referenced supports 710. Optionally, stand 770 is provided on a rotatable plate (e.g. manual or motorized) so as to enable image capture from multiple observation angles.

Optionally, camera unit 720 permits imaging of a top of a head and shoulders of a subject, for example, by being elevatable and aimable down.

In order to capture images of external body surfaces using posing stand 770, the subject is typically at least partly undressed.

Figure 8A:
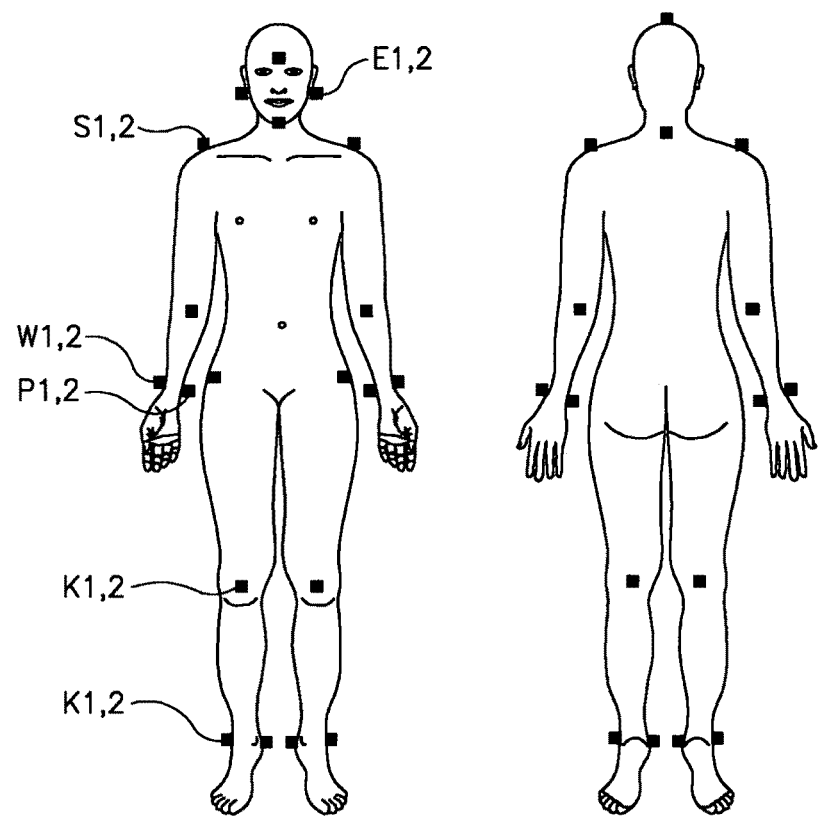
FIGS. 8A and 8B illustrate salient body locations with attached reflective fiducials in accordance with some exemplary embodiments of the invention and a representative skeletal model constructed on the basis of analysis of images including the fiducials respectively.

FIG. 8A illustrates reference points distributed over the entire body according to an exemplary embodiment of the invention. The reference points may include, for example, center point between eyes, ear lobes, chin point, shoulder tips, inner and outer elbow tips, wrist tips, pelvic bone tips, knee tips and ankle tips. In an exemplary embodiment of the invention, the reference points are marked. Optionally, fiducial markers (e.g. reflective stickers) are placed at the marked points. Once the fiducial markers are placed, the subject is first positioned in a preferably standing pose on the indexed floor mat against the uniform color backdrop of stand 770. Arm and hand supports 710 are positioned to suit the subject height and width. Arms are best positioned in an angle relative to the torso so as to enable optimal image captures, whereby a sufficient number of fiducials appear in adjoining images so as to enable proper mapping of all pixels in all subsequent images to a common coordinate system.

Figure 8B:
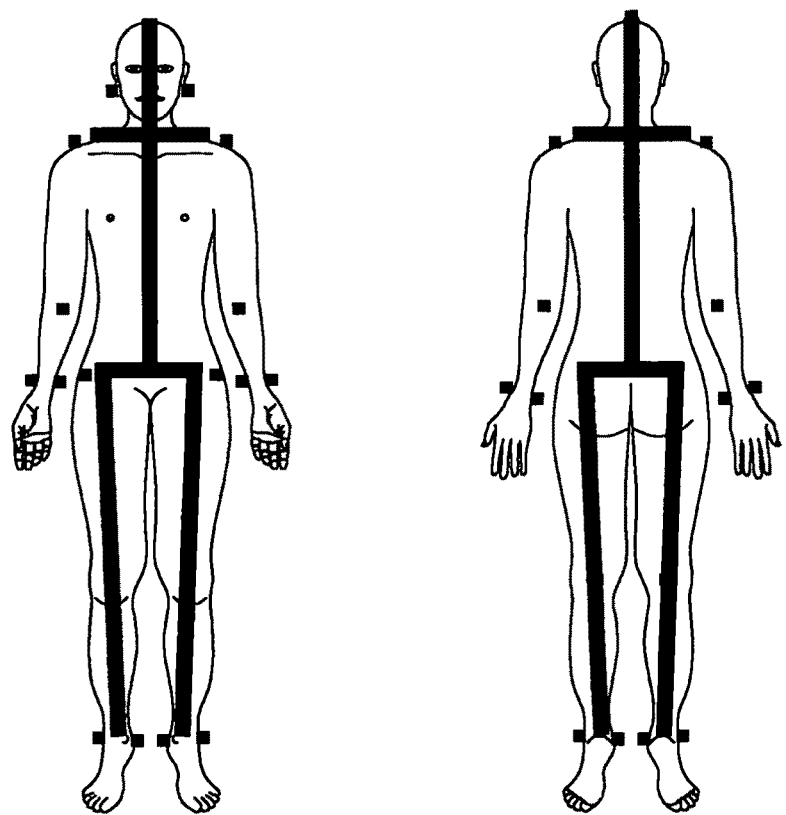

FIG. 8B illustrates that after a series of images including the fiducial markers have been captured; a skeletal framework (heavy black lines) can be generated based on the fiducial locations. This skeletal framework can be used in the planning of an image capture scheme based upon smaller fields of view. In an exemplary embodiment of the invention, each captured image contains at least 1, optionally 2 or 3 or more fiducial markers and overlapping images are aligned based upon the fiducial markers. In this way, a composite image of the subject can be constructed. Optionally, this provides a unified coordinate system for all the imagery captured over a person's body.

In an exemplary embodiment of the invention, an image capturing procedure is controlled by a controller. According to various exemplary embodiments of the invention, the controller may be mechanical, electronic, electromechanical, robotic or combinations thereof. Optionally, images of the whole body of the subject are first captured using a wide field of view and low resolution, detecting the body contour, and optionally all the observable fiducials, using a spatial filter F (e.g. Difference of Gaussians; DOG) followed by a threshold T. This calculation segments (S) the whole body from the background differencing R from B. This procedure is one exemplary embodiment of enhancement processing 120.

In an exemplary embodiment of the invention, images of portions of the body of the subject are captured at a magnification and/or resolution selected to aid in analysis of lesions/moles of a designated minimum size. Exemplary designated minimum sizes are 1, 2, 3, 4 and 5 mm diameter or lesser or greater or intermediate sizes. Optionally, the controller automatically moves one or more cameras to an adjacent field of view after each image is captured. Optionally, adjacent fields of view overlap.

Flexibility with Respect to Color System

Typically, color coordinate systems which employ color components as the fundamental representation of the image are generally considered a basic representation of an image and all other representations are considered derivatives thereof.

In different exemplary embodiments of the invention, different image processing methods are applied to color images represented in various color coordinate systems. These coordinate systems include, but are not limited to, systems which employ color components (e.g. RGB, CMY) and systems which employ luminance (i.e. Luma) and chrominance (i.e. Chroma) components (e.g. Lab, HSB, YUV, and YCrCb).

In some exemplary embodiments of the invention, one or more of the color values R, G, B and Y may be replaced by components of alternate image representations such as, for example, H, S, B, L, a, b, U, V, Cr, Cb, C and M. It should be noted that the precise identification of the color components depends on the sensitivity curves of the detectors used. In an exemplary embodiment of the invention, the acquired image may be corrected prior to processing. Alternatively or additionally, the processing is optionally modified to take into account the individual spectral sensitivity of the sensor used.

A simple determination of Luminance (L) is not considered a PCF because the function of L is to transform color data into grayscale data. Despite this exclusion, some exemplary PCFs include L in conjunction with other terms indicative of color.

In those exemplary embodiments of the invention, which employ color component representations, such as RGB, the PCF may include at least two of R, G and B data.

In those exemplary embodiments of the invention, which employ Luma and Chroma component representations, such as Lab, the PCF may include, for example:

L and a or b; and/or
one or more of a and b.

For purposes of this specification and the accompanying claims, the term "a" is considered indicative of green or red saturation and the term "b" is considered indicative of blue or yellow saturation.

EXAMPLES

The following illustrative examples are presented to highlight exemplary capabilities of different embodiments of the invention in different clinical contexts. While each example is described in detail, the details should not be construed as limits with regard to the particular clinical context depicted.

Materials and Methods

Endoscope: The CF-Q240Z, PCF-Q240Z, Olympus Optical Co. Ltd, Tokyo Japan, model endoscope was used in the examples of FIGS. 12, 13, 14, 15 and 16 and 17.

Light source: A standard white light flash as used in digital cameras for the images of FIGS. 9 and 10.

Figure 12A:
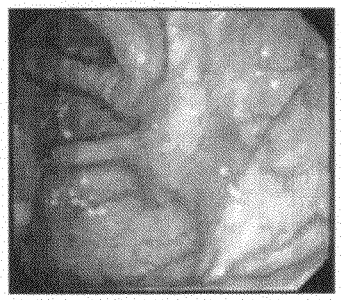
FIG. 12A is an image acquired using an endoscope and auto florescence detection of a field of view including a flat adenoma.

For FIG. 12A, Afi imagery with Xenon 395-475 nm, via RGB rotary filter and collection on color filter switched monochromatic CCD, was used.

For FIGS. 12, 13, 14, 15 and 16 and 17 an NBI light source with narrow bands at 415, 445, 500 nm, CF-Q240Z, PCF-Q240Z, Olympus Optical Co. Ltd, Tokyo Japan, was used. The spectra is narrow bands at 415, 445, 500 nm.

For FIG. 15, standard typical endoscopy equipment with RGB white light (typically xenon) was used.

Example 1

Detection of Ectopic Abnormalities

FIGS. 9, 10 and 11 illustrate application of an exemplary enhancement processing method 120 to detection and/or analysis of ectopic skin lesions.

Figures 9A, 9B, 9C, 9D, 9E, 9F:
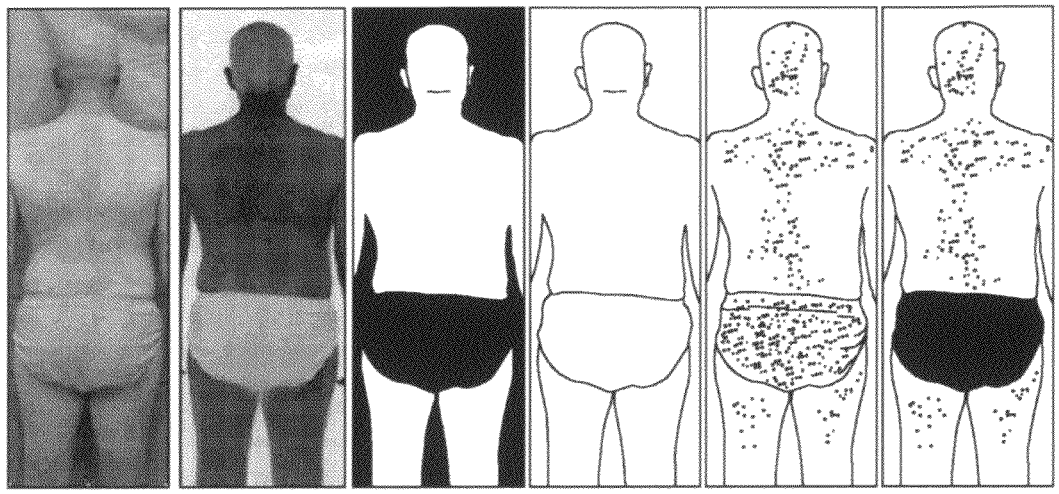
FIGS. 9A, 9B, 9C, 9D, 9E and 9F depict a series of stages in an exemplary method according to some embodiments of the invention which process images of an external surface of the body to identify moles and/or lesions.

FIGS. 9A; 9B; 9C; 9D; 9E and 9F are a series of images illustrating a sequence of intermediate results of a high resolution mole/lesion detection method which relies upon an exemplary embodiment of enhancement processing 120. All panels in this and subsequent figures are presented here as grayscale images, although the actual image capture and analysis employs RGB images. The sequence of images follows exemplary image processing approach 1 (300) as detailed hereinabove and depicted in FIG. 3.

FIG. 9A depicts the "G" channel of an RGB image resulting from PRP 312.

FIG. 9B depicts the same field of view with the PCF (R−G) applied to produce PCFI 320.

FIG. 9C depicts the same field of view segmented with PCF (R−B) applied, a bi-modal histogram H distribution (350) and thresholding T (360) to produce segmented image S (380).

FIG. 9D depicts the body segmented contour of FIG. 9C.

FIG. 9E depicts the same field of view in the form of a detection map resulting from the PCFI of FIG. 9B.

FIG. 9F depicts the detection map of FIG. 9E intersected with segmented image S of FIG. 9C.

The result of this exemplary enhancement processing 120 is to increase the visibility and/or detection of moles and/or lesions on the back of the subject relative to a standard color (e.g. RGB) digital image. Optionally, the increased visibility aids in diagnosis and/or identification of lesions suitable for biopsy and/or monitoring of lesion progression (either generally or for specific lesions).

While the entire back of the subject is presented here as a single image for clarity, each panel in FIG. 9 optionally represents a series of color images that are captured (for example, in RGB format) and aligned using fiducial markers and stored in a computer memory. Display 150 on display 250 at a desired resolution and/or magnification involves constructing a composite image of appropriate fields of view.

In an exemplary embodiment of the invention, camera calibration is performed prior to the imaging process. Calibration may be in terms of, for example, one or more of color, responsivity, non-uniformity correction, and bad pixel masking. Optionally, global and/or local skin tone estimations are performed based on a color reference tablet. The tablet can be located, for example, on positioning stand 770.

In exemplary embodiments of the invention, detection of skin moles and/or lesions by enhancement processing 120 includes one or more filters F.

In an exemplary embodiment of the invention, Filters F include NABPF such as Difference of Gaussians (DOG) and/or Difference of Boxes (DOB). Optionally, F can be applied at different spatial scales detect lesions which meet a threshold criteria T. Optionally, T is a locally adaptive threshold. In this exemplary embodiment, an adaptive T is applied to a NABPF to impart adaptivity. In other exemplary embodiments of the invention, a constant T is used in conjunction with an ABPF. These two possibilities are not equivalent due to nonlinearity of the operations. In an exemplary embodiment of the invention, a Constant False Alarm Rate (CFAR) threshold is employed in order to reduce the incidence of false positives. Optionally, the CFAR normalizes the output of the NABPF or ABPF detection filter by a local deviation measure, thereby providing a locally adaptive threshold. A non adaptive T is one which is computed for the statistic of the entire image. An adaptive T is one which is computed locally within the image so as to provide local adaptation.

Optionally, additional lesion criteria are employed. For example, the "ABCD" (Asymmetry, Border irregularity, Color variability, and Diameter) rule can be employed. Any skin abnormalities which meet threshold criteria applied to filtered data are then categorized in terms of the computed measures, at various levels of abnormality. In an exemplary embodiment of the invention, each level of abnormality is indicated on the image, for example by coloring it a distinctive color.

In an exemplary embodiment of the invention, enhancement processor 230 reduces interference from hair with respect to detection of skin moles and/or lesions. Moles and lesions are often pigmented black and/or brown and/or pink and/or red and reflect light accordingly.

Black hair is typically characterized by low light reflectivity in all color bands. This can cause "false positives" in dark lesion detection, or can obstruct actual lesions and moles resulting in increased "true negatives".

Light hair such as blond, red hair, and grayed hair reflect more strongly, and therefore can cause "false positives" in lesion detection.

Optionally, contrast variations in the Green or Luminance plane, and color variations between adjoining pixels of lesions is employed to overcome these two types of interference from hair. For example, the color differencing scheme, in conjunction with a sufficiently large high pass or band pass filter, described hereinabove with respect to FIG. 9 can serve to both reduce hairline interference and enhance lesions/moles.

Figures 10A, 10B, 10C:
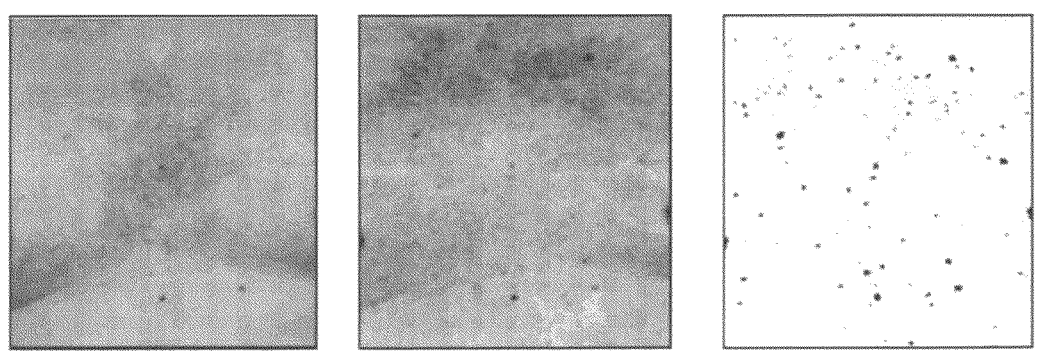
FIGS. 10A, 10B and 10C illustrate an exemplary method according to some embodiments of the invention which process images of an external surface of the body to eliminate interference caused by body hair.

FIGS. 10A, 10B and 10C depict an example of a hairy area of a male chest, whereby some moles, lesions and blemishes are obstructed by dark hair which could potentially cause false positives.

FIG. 10A depicts the "G" channel of an RGB image resulting from PRP 312.

FIG. 10B depicts the same field of view with the PCF (R−G) applied to produce PCFI 320. This image processing removes hair lines and the suspected moles and lesions remain in the processed image.

FIG. 10C depicts the result of the detection process (analogous to that described for FIG. 9F). Moles and lesion in the area covered by hair in FIG. 10A are as apparent as those in portions of the field of view which are hairless.

Optionally, lesion and mole detection processing as generally described above includes decomposition into several resolution scales. Optionally, each resolution scale is processed separately and combined to generate a detection map of lesions and moles (e.g. FIGS. 9F and 10C). Decomposition contributes to cost effective detection of various sizes of lesions and moles within a single enhancement processing 120.

In an exemplary embodiment of the invention, the following processing sequence is applied to one or more of the registration scales.

FIGS. 11A and 11B depict matching of detection maps acquired from a same subject at different times. In an exemplary embodiment of the invention, matching begins with the most prominent detected abnormalities (indicated by (1)), and then considers progressively less prominent abnormalities (indicated by 2 and 3).

Referring again to FIGS. 9A, 9B, 9C, 9D, 9E and 9F, as well as to FIG. 3, an exemplary enhancement processing 120 algorithm is described in greater detail.

The exemplary algorithm employs 3 PCFI terms (320)
PCFI1=G−R
PCFI2=B−R
PCFI3=G The exemplary algorithm employs a filter F (330) which is a High Pass Filter (HP) designed to pass the largest size lesion or mole for the respective scale. HP has zero mean, thereby locally and globally clamping the output image to zero mean.

According to the exemplary algorithm, PCFO (340) is the product of the three PCFI terms multiplied by F:

$$PCFO1=F1((PCFI1)^{GRE})*F1((PCFI2)^{BRE})*F1((PCFI3)^{GE})$$

Where
GRE=Green-Red difference image exponent.
BRE=Blue-Red difference image exponent.
GE=Green image exponent.
F1=High pass filter.

The respective exponent values optionally provide relative weighting of the respective PCFIs, and can be determined as a function of maximized detection statistics in a referenced image database. Typical exponent values may range between 1-3.

An additional filter (F2), optionally a NABPF (e.g. DOG or Laplacian of Gaussians as an approximation to DOG) can be applied:

$$F2=GSS(LP(GS))$$

where GS is a two dimensional Gaussian filter convolution kernel with Standard Deviation (SD) proportional to the lesion or mole being detected. For example, the SD of 6 pixels may be used when detecting lesions and moles of the size of several pixels diameter.

The filter may be implemented in a separable fashion so as to enable fast computing; and Where LP is a two dimensional 3×3 Laplacian filter convolution kernel [0,−1,0; −1,4,−1; 0,−1,0]; and where GSS is a two dimensional Gaussian filter convolution kernel with an SD which provides a local smoothing of intermediate filtering results prior to a thresholding operation.

The result of filtering F2 applied to the result of PCFO1 is defined as PCFO2:

$$PCFO2=F2(PCFO1)$$

Application of a threshold T (FIG. 3) imposes pixel based thresholding whereby a local or global SD of the image histogram is computed, and used in setting the threshold, for example THR=K*SD, where typically K varies between K=2-3 produces the following equation 1:

$$O=POP(D(E, S(L(T(H(F2(PCFO1(F1(PCFI(PRP(I))))))))))) \quad (1)$$

Equation 2, below, illustrates another embodiment whereby the filter F1 is applied to the PCFI1s prior to raising them to their respective powers, $$PCFO1=(F1(PCFI1))^{GRE}*(F1(PCFI2))^{BRE}*(F1(PCFI3))^{GE} \quad (2)$$

and used in Equation 1.

When enhancing or detecting lesions which are not well defined spatially, and when enhancing and detecting inflammations which typically do not have well defined dimensions as they tend to spread over large areas of skin albeit at low contrast, the filter F2 is optionally selected to be an ABPF.

The three images resulting from the three terms in the PCFO1 expression typically represent contrast moles and lesions by lower (darker) values, and skin tone values by higher (lighter) values.

In the resulting detection pixel map darker pixel values represent higher likelihood that the respective lesion or mole is clinically significant.

The filter F2 is used as a detection filter and is typically characterized by a DOG (estimated above by the Laplacian of Gaussian) or a DOB. This bandpass filter is optionally matched to the size of the lesions and moles being detected in the respective resolution scale of the image pyramid. Optionally, several NABPFs (e.g. DOG) of varying sensitivities are employed to detect various sizes of lesions and moles. Histogram analysis is optionally used for determining threshold levels.

The histogram of the resulting F2(PCFO1( . . . )) image is optionally computed, from which the SD is optionally computed, and a threshold K*SD is optionally computed and applied to the map. Optionally, the applied threshold varies with the standard deviation (SD) and/or the mean of the histogram.

Pixels below the threshold (i.e. negative values falling below the threshold), are designated as suspected locations of lesions and moles, and the detection map D is generated. The detection map now represents connected blobs which are labeled and analyzed in terms of various features, including mean value, SD, size, shape, color, and a boundary localization operation follows to define the precise boundary of each blob. Blob feature vectors are computed for all candidate blobs and stored for further analysis. These vectors may also be characterized in accordance with definitions of the well-known ABCD criteria of suspected moles. If T1, T2, . . . Tn represent scale space representations of the thresholded F2(PCFO1( . . . )) detection maps, then the L operation performs various logical operations on the T maps, such as for example "OR"ing the maps:

$$L=(T1)OR(T2)OR \ldots (Tn) \quad (3)$$

In another exemplary embodiment of the invention, in expressions for PCFO1, the image plane G in the first term in the equations is replaced by luminance L, which is derived from the RGB image per pixel.

Another improved embodiment of the above processing procedure is provided whereby the power function is replaced by Lookup Tables (LUT) representing the power operation, thereby simplifying and accelerating the computation. A LUT of pre-computed values avoids the need to compute power computations which are expensive in terms of short term processor load.

The constant exponents GE, GRE and BRE, or their respective LUTs, may be determined by the use of a calibration set of images derived from subjects, and the optimization of the parameters to these images using learning algorithms which modify the parameters as a function of success and failure detection statistics in reference imagery.

Example 2

Exemplary Embodiment of Invention Compared to Autofluorescence in Detection of Flat Adenoma (Tumor)

FIGS. 12A, 12B, 12C, 12D, 12E, 12F, 12G and 12H illustrate that an exemplary enhancement processing 120 algorithm according to embodiments of the invention can serve in place of auto-fluorescence detection for flat adenoma. Flat adenoma (e.g., in colon tissue) presents special problems in detection because it typically lies slightly below the surface. Use of Red light is often inappropriate as it penetrates too deeply. Use of blue light is often problematic because it does not penetrate sufficiently.

FIG. 12A is an image acquired using an endoscope and auto florescence detection of a field of view including a flat adenoma. The flat adenoma is discernible in the central part of the image as a large dark region.

Figure 12B:
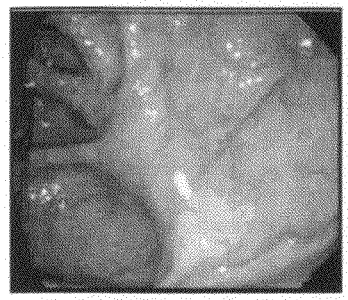
FIG. 12B is an un-enhanced RGB image of the same field of view as FIG. 12A.

FIG. 12B is an un-enhanced RGB image of the same field of view as FIG. 12A. As expected, the flat adenocarcinoma is not discernible.

Figure 12C:
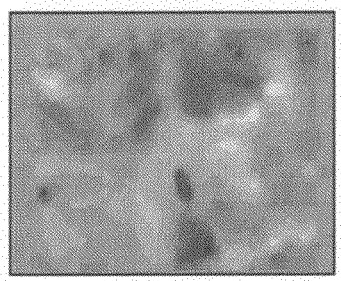
FIGS. 12C and 12D depict spatially filtered Lab a and Lab b components respectively according to an exemplary embodiment of the invention to the field of view of FIG. 12A.
Figure 12D:
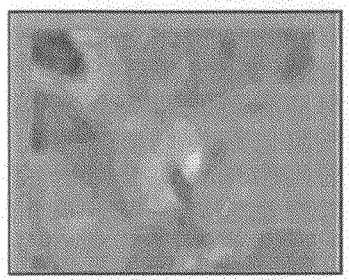

FIGS. 12C and 12D depict Lab a and Lab b components respectively after application of an adaptive band pass filter (ABPF) according to an exemplary embodiment of the invention to the field of view of FIG. 12A. The flat adenocarcinoma is slightly discernible near the center of the field of view at this stage.

Figure 12E:
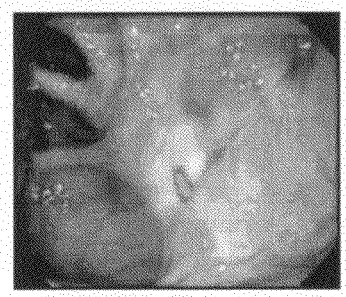
FIG. 12E is a Lab image of the field of view of FIG. 12A with an L component enhanced according to an exemplary embodiment of the invention.

FIG. 12E is a Lab image of the field of view of FIG. 12A with an enhanced L component (EL=L+2*ab; color enhancement also optionally enabled by using histogram stretched ABPF outputs for a and b components) according to an exemplary embodiment of the invention. The tumor appears more prominently as a result of this additional enhancement processing, although its borders are not clearly defined. In a color image, the enhanced a and b components (Ea, Eb) are optionally enhanced via Ea=a+H(ABPF(a)), where H is preferably a DRSLUT dynamic range stretching look up table determined by the histogram distribution of s a function of the available display dynamic range.

Figure 12F:
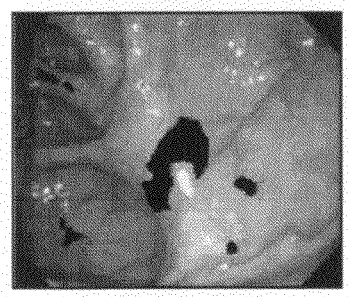
FIG. 12F-12H are detection maps of the field of view of FIG. 12A generated by applying various image processing techniques according to exemplary embodiments of the invention.

FIG. 12F is a detection map of the field of view of FIG. 12A generated by applying a threshold to ABPF (a)*ABPF (b), where a and b are color components of Lab. The borders of the adenocarcinoma are clearly defined by application of this ABPF.

Figure 12G:
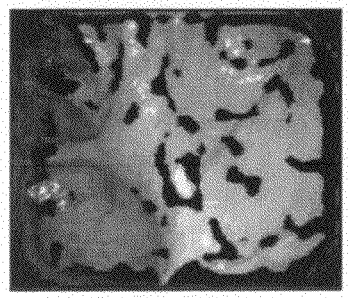

FIG. 12G is a detection map of the field of view of FIG. 12A generated by applying a threshold to DOG (a)*DOG (b), where a and b are color components of Lab, and DOG is slightly small and mismatched to adenoma dimensions. Use of an NABPF produces definition of the adenocarcinoma borders relative to FIG. 12F and may cause many false positive regions to appear in the image.

Figure 12H:
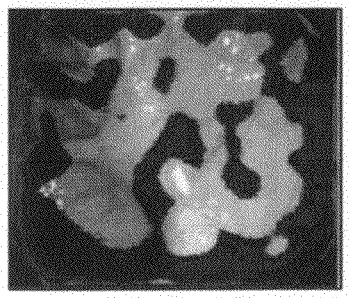

FIG. 12H is a detection map of the field of view of FIG. 12A generated by applying a threshold to DOG(a)*DOG(b), and DOG is slightly larger than in FIG. 12G and mismatched to adenoma dimensions. Use of an NABPF produces definition of the adenocarcinoma borders relative to FIG. 12F and may cause many false positive regions to appear in the image. It should be noted that the borderlines have shifted due to the increased extent of the distance between pixels used in the filtering operation.

In summary, these graphic results show that enhancement processing 120 is as sensitive as, or higher sensitivity, than auto fluorescent detection for flat adenoma. Alternatively or additionally, these results show that use of an adaptive bandpass filter increases sensitivity and/or accuracy of flat adenoma detection relative to a non adaptive bandpass filter.

Example 3

Exemplary Embodiment of Invention Compared to Narrow Band Imaging (NBI) in Detection of Colorectal Lesions FIGS. 13A, 13B, 13C, 13D, 13E and 13F illustrate that an exemplary enhancement processing 120 algorithm according to embodiments of the invention can serve in place of auto-fluorescence detection for adenoma. In an exemplary embodiment of the invention, the lesion being searched for is a view of a faint (redish) lesion with loss of capillary pattern, and of diameter 7 mm, in the normal sigmoid colon.

Figure 13A:
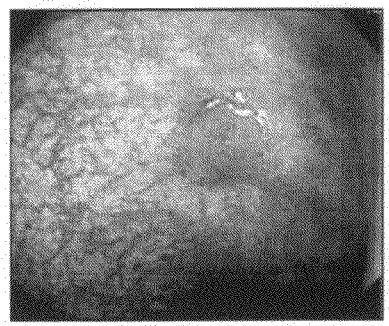
FIG. 13A is an unenhanced image of a flat adenoma acquired with a narrow band infrared (NBI) endoscope.

FIG. 13A is an unenhanced image of a flat adenoma acquired with a narrow band infrared (NBI) endoscope. The colorectal lesion is barely discernible near the center of the field of view.

Figure 13B:
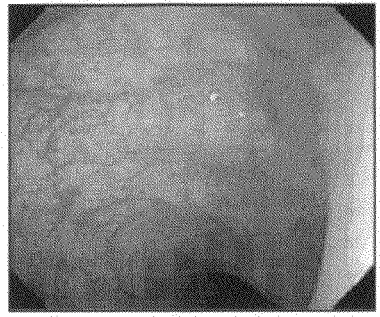
FIG. 13B is an RGB image of the same field of view as FIG. 13A.

FIG. 13B is an RGB image of the same field of view as FIG. 13A with no enhancement processing applied. The colorectal lesion is not discernible.

Figure 13C:
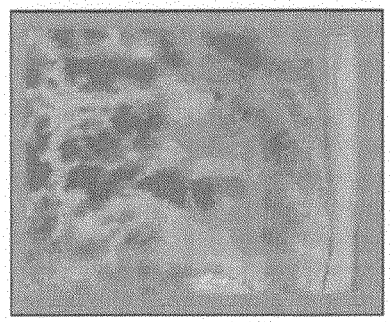
FIGS. 13C, 13D and 13E depict various Lab component images of the same field of view as FIG. 13A.

FIG. 13C depicts the Lab a-component of the same field of view as FIG. 13A after application of an ABPF according to an exemplary embodiment of the invention. The colorectal lesion is not clearly discernible.

Figure 13D:
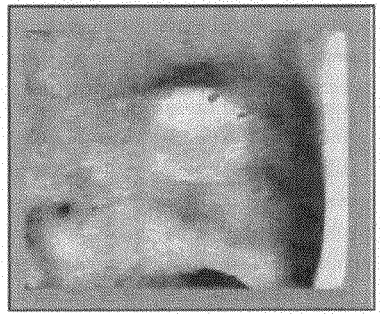

FIG. 13D depicts the Lab b-component of the same field of view as FIG. 13A after application of an ABPF according to an exemplary embodiment of the invention. The colorectal lesion is clearly discernible and variations within the lesion are apparent. These variations are not seen in the NBI image of FIG. 13A. This may be determined by pigments found in the lesion and/or layers over the lesion.

Figure 13E:
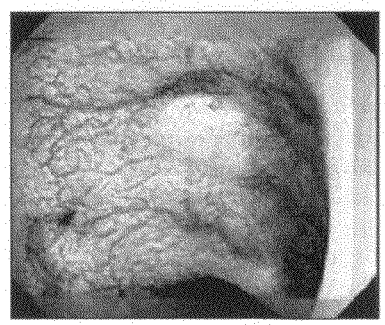

FIG. 13E is an Lab image of the field of view of FIG. 13A with an enhanced L component (EL=L+ab; color enhancement optionally enabled by using histogram stretched ABPF outputs for a b components) according to an exemplary embodiment of the invention. In this image, resolution of blood vessels is increased, but lesion borders are less clear in comparison to FIG. 13D.

Figure 13F:
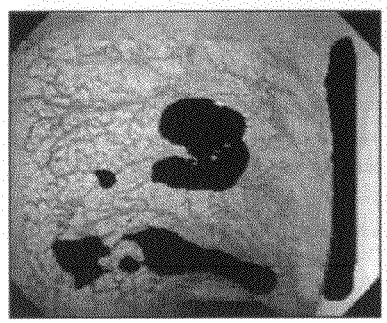
FIG. 13F shows a detection map of the field of view of FIG. 13A according to an exemplary embodiment of the invention.

FIG. 13F is a Detection map of the field of view of FIG. 13B generated by applying a threshold to the image of FIG. 13. D. The lesion is clearly defined with sharp borders as a result of the thresholding.

In summary, these graphic results show that enhancement processing 120 is (at least) equivalently sensitive to NBI detection for colorectal lesions visualization.

Exemplary enhancement processing 120 in Examples 2 and 3 is implemented with standard white light. This can reduce equipment cost relative to auto fluorescence and/or NBI based detection. In some cases, medical users find it simpler to perform an endoscopy procedure using a single lighting mode as opposed to switching between a viewing light and an analytic light. In some cases, the use of a white light endoscope allows additional tools and/or components to be used, as compared to an NBI or NBI/RGB endoscope, for example, due to space, interface, spatial configuration and/or connection considerations.

Example 4

Additional Exemplary Embodiment of Invention Compared to Narrow Band Imaging (NBI) in Detection of Colorectal Lesions FIGS. 14A, 14B, 14C, 14D, 14E and 14F illustrate that an exemplary enhancement processing 120 algorithm according to embodiments of the invention can serve in place of NBI detection for colorectal lesion. As in example 3, this lesion is also a colorectal lesion, however it is much smaller spatially, and is of considerably lower contrast in the resulting NBI image, as compared to the previous example.

Figure 14A:
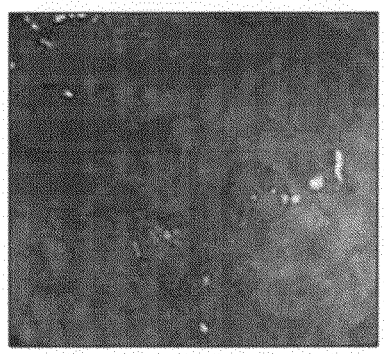
FIG. 14A is an unenhanced image of a flat adenoma acquired with an NBI endoscope.

FIG. 14A is an unenhanced image of a colorectal lesion acquired with an NBI endoscope. The lesion is hardly discernible, even with NBI imaging.

Figure 14B:
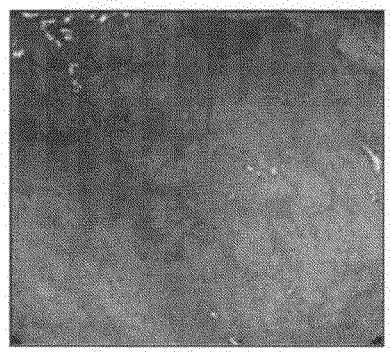
FIG. 14B is an RGB image of the same field of view as FIG. 14A.

FIG. 14B is an RGB image of the same field of view as FIG. 14A. As expected, the lesion is not discernible.

Figure 14C:
FIGS. 14C, 14D and 14E depict various Lab component images of the same field of view as FIG. 14A.

FIG. 14C depicts the Lab a-component of the same field of view as FIG. 14A after application of an ABPF according to an exemplary embodiment of the invention. The lesion is not discernible at this stage.

Figure 14D:
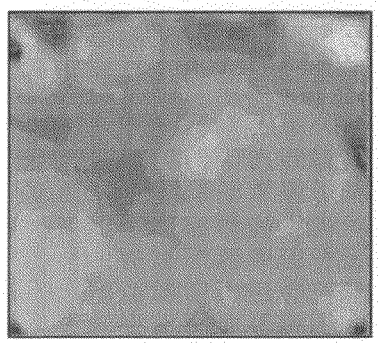

FIG. 14D depicts the Lab b-component of the same field of view as FIG. 14A after application of an ABPF according to an exemplary embodiment of the invention. The lesion is barely discernible as a white spot near the center of the field of view.

Figure 14E:
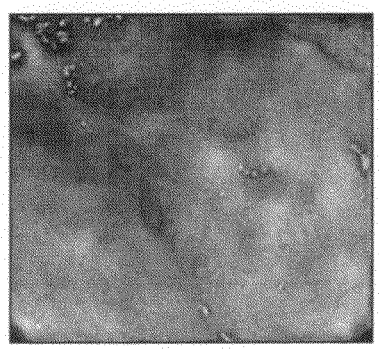

FIG. 14E is an Lab image of the field of view of FIG. 14A with an enhanced L component (EL=L+ab; color enhancement optionally enabled by using histogram stretched ABPF outputs for a and b components) according to an exemplary embodiment of the invention. Discernability of the lesion is less than in FIG. 14D.

Figure 14F:
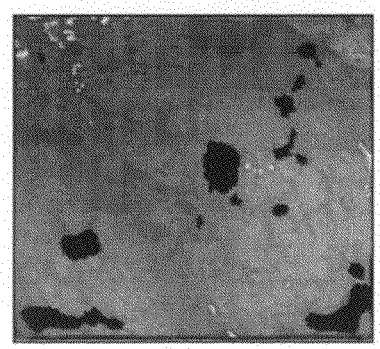
FIG. 14F is a Detection map of the field of view of FIG. 14A.

FIG. 14F is a Detection map of the field of view of FIG. 14A generated by applying a threshold to $(ABPF(a))^1 * (ABPF(b))^1$, where a and b are color components of Lab. The entire lesion area is marked by the detected (black) spot with clearly defined borders.

This example illustrates the ability of exemplary enhancement processing algorithms according to embodiments of the invention to reveal suspected lesions even where NBI imaging is unable to detect the tumors.

Example 5

Conversion of RGB Image to Lab Image Followed by Processing for Enhancement, Analysis and/or Detection of Early Cancer FIGS. 15A, 15B, 15C, 15D, 15E, 15F, 15G and 15H illustrate that an exemplary enhancement processing 120 algorithm according to embodiments of the invention can be employed in three modes for early cancer detection. Early cancer detection is associated with very low contrast lesions (in both luma and chroma), which results in increased false positives in the detection process, and difficulties in determining the borderlines of the effect. In order to achieve early detection and effective biopsy collection, the user may prefer to operate sequentially in three modes of operation.

Figure 15A:
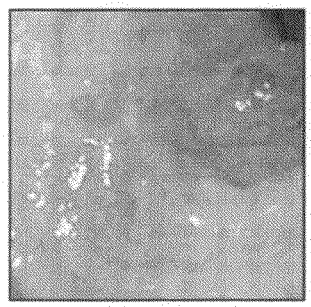
FIGS. 15A-15D depict various Lab and Lab component images of a field of view including an early stage tumor.

FIG. 15A depicts the L component of an Lab image of a field of including an early stage tumor. The enhance mode provides improved contrast of visually undiscernable lesions over the entire image. Upon a suspected lesion, the user may direct the camera field of view towards that lesion area, and switch to analyze mode, whereby the analysis applies detection processing of higher sensitivity and specificity since it assumes there is a suspected lesion in that area. The user may also activate the detect mode, whereby such detection operation is applied to the entire image, albeit optionally at lower sensitivity and specificity, for example to compare the result of the suspected lesion to the rest of the image. Detection mode may also be applied to the entire image continuously. It should be noted that detect and/or analyse may use absolute thresholds and/or be relative to values in the rest of the image (e.g., by assuming that the size of the lesion is small relative to the image).

The tumor is hardly discernible in the L component, but is clearly discernible in the color image. However, the borderlines of the cancerous growth are not clear, and the areas of highest angiogenesis activity are also not clearly defined.

Figure 15B:
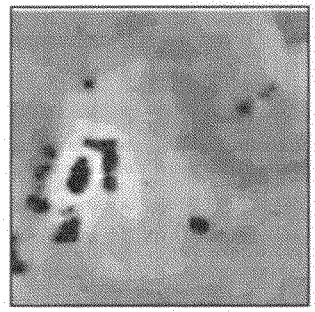

FIG. 15B depicts the a component of an Lab image of a field of including an early stage cancer. While the cancer is vaguely discernible, its borders are not well defined.

Figure 15C:
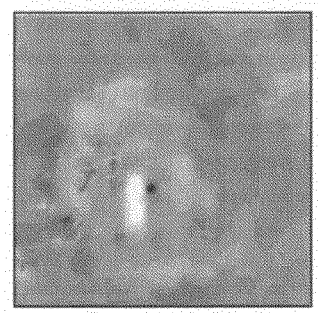
Figure 15D:
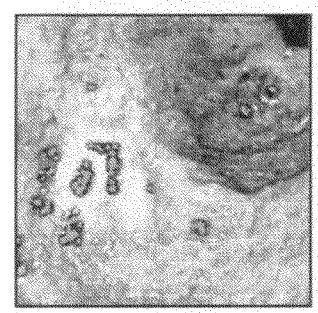

FIG. 15C depicts the b component of an Lab image of a field of including early stage cancer. While the cancer is vaguely discernible, its borders are not well defined FIG. 15D is an Lab image of the field of view of FIG. 15A with an enhanced L component (EL=L+k*ab; color enhancement optionally enabled by using histogram stretched ABPF outputs for a and b components) according to an exemplary embodiment of the invention. At this stage, the cancer discernability may be less than in FIGS. 15B and 15C, due to the cluttering effect of the L component.

Figure 15E:
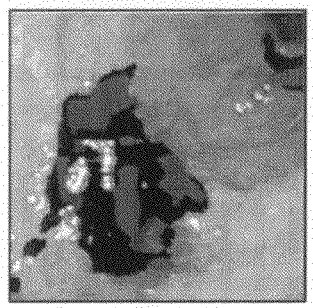
FIGS. 15E-15H show detection maps according to an exemplary embodiment of the invention generated by applying various thresholds to images of a field.

FIG. 15E is a detection map according to an exemplary embodiment of the invention generated by applying a threshold to $(ABPF(a))^1*(ABPF(b))^1$, where a and b are color components of Lab and where $(ABPF(a))^1$ and $(ABPF(b))^1$ are detection maps of varying sensitivity with the darker map indicating the tumor and the lighter map indicating the areas of higher activity ("hot spots") within the cancerous region. This exemplary enhancement processing reveals the tumor with sharp borders and divides it into regions. The depicted regions are believed to each have a clinical significance. Borderlines and "hot spot" areas may be important sites for collecting biopsies.

Figure 15F:
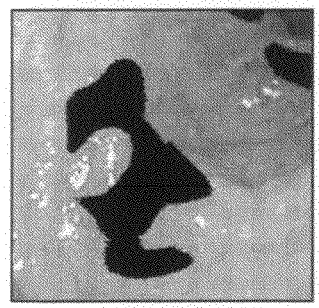

FIG. 15F is a DOG detection map according to an exemplary embodiment of the invention generated by applying a threshold to the $PCFO=(DOG(a))^1*(DOG(b))^1$, where a and b are color components of Lab. The generally poor localization of the borderlines may be noted.

Figure 15G:
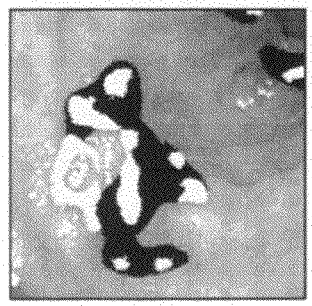

FIG. 15G is a DOG detection map according to an exemplary embodiment of the invention generated by applying a threshold to the map of FIG. 15F. The dark region depicts the area detected by the PCFO with the large scale NABPF DOG parameters (center SD=10, surround SD=20), and the light regions depict the areas detected by the PCFO with small scale DOG parameters (center SD=5, surround SD=10). Some of the small scale areas are included within the large scale area, and some others are located outside the area of the large scale DOG although in close proximity. By logically combining the respective areas, for example, by the L function as described above into one area based on one or more of geometrical inclusion, overlapping and proximity considerations, one may recover the borderlines as achieved by the ABPF. In another logic of combination, if a small region is identified within a larger region and near or at an edge thereof, this is taken as an indication that the area is an active area and should be sampled (e.g., biopsy). If the small area is outside the large area, but near an edge the space between may be bridged, for example, following additional analysis of the colors or based on analysis of the sizes and distances between the regions. Optionally, threshold numbers and/or other decision functions are preconfigured into the system. In another example, provision of multiple small areas within a certain range (e.g., threshold or dependent on number of regions) is used as an indication that they should be combined. In another example, if a region is identified using multiple filters this is taken as an indication of increased reliability of the result.

Figure 15H:
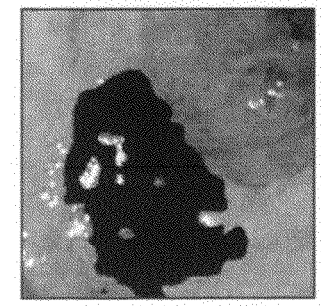

FIG. 15H is a detection map generated by applying a PCFI comprising [(R−G)*(G−B)], without any filter. A threshold is applied directly to the PCFI data. The map of FIG. 15H defines more pixels as belonging to the tumor than the maps of FIGS. 15F and/or 15G. This suggests that use of a filter can reduce false positive results in defining the borderlines.

FIG. 15D represents enhance mode output, and FIGS. 15E-15H represent analyze and detect mode outputs.

Example 6

Figure 16A:
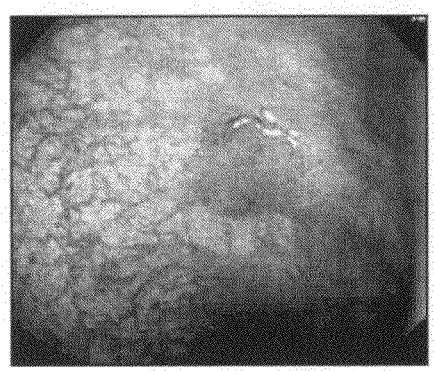
FIGS. 16A and 17A are narrow band infrared (NBI) endoscopic images.
Figure 17A:
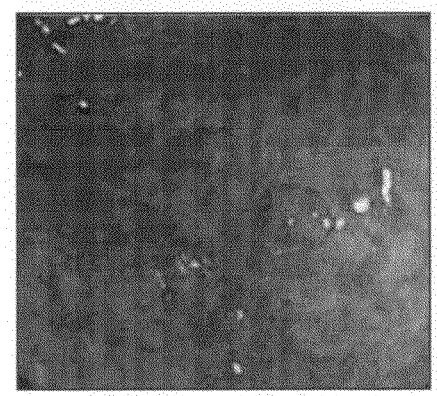

Application of Exemplary Enhancement Processing Algorithms According to Embodiments of the Invention to NBI Images FIGS. 16A and 17A are unenhanced narrow band infrared (NBI) endoscopic images (e.g., as described in examples 3-4, above).

Figure 16B:
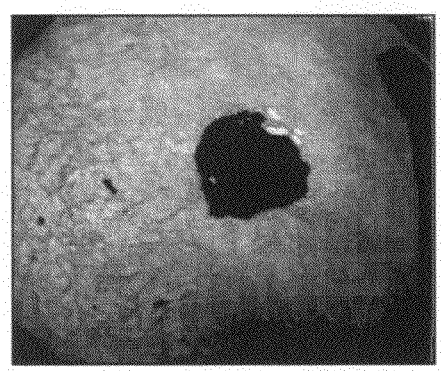
FIGS. 16B and 17B are NBI images as in FIGS. 16A and 17A respectively enhanced using exemplary algorithms according to embodiments of the invention.
Figure 17B:

FIGS. 16B and 17B are NBI images as in FIGS. 16A and 17A respectively enhanced using exemplary algorithms according to the present invention. The NBI images are first converted to Lab, then an ABPF is applied to the a and b components, and the PCFO=ABPF(a)*ABPF(b) is further thresholded, whereby the extreme high values in the global histogram are thresholded and shown as the darkly mapped pixels. It should be noted that the algorithm detected both the clearly visible lesion, as well as the side of the hardly discernible lesion, thereby potentially improving the effectiveness of NBI image usage.

This indicates that enhancement according to exemplary embodiments of the invention improves tumor discernability in NBI images as well as conventional RGB or Lab images.

These examples, together with the theoretical description presented hereinabove, demonstrate that exemplary embodiments of enhancement processing 120 have demonstrable clinical utility.

General

Systems, methods and algorithms according to various embodiments of the invention rely upon execution of various commands and analysis and translation of various data inputs. Any of these commands, analyses or translations may be accomplished by software, hardware (e.g., in the form of dedicated systems or programmable systems) or firmware according to various embodiments of the invention. In an exemplary embodiment of the invention, machine readable media contain instructions for one or more image processing algorithms as described above are provided. In an exemplary embodiment of the invention, enhancement processor 180 executes instructions for one or more image processing algorithms as described above.

The present invention has been described using detailed descriptions of embodiments thereof that are provided by way of example and are not intended to necessarily limit the scope of the invention. In particular, numerical values may be higher or lower than ranges of numbers set forth above and still be within the scope of the invention. The described embodiments comprise different features, not all of which are required in all embodiments of the invention. Some embodiments of the invention utilize only some of the features or possible combinations of the features.

Alternatively or additionally, portions of the invention described/depicted as a single unit may reside in two or more separate physical entities which act in concert to perform the described/depicted function. Alternatively or additionally, portions of the invention described/depicted as two or more separate physical entities may be integrated into a single physical entity to perform the described/depicted function.

Alternatively or additionally, portions of the invention described/depicted as a process or step may be divided into two or more separate processes or steps which act in concert to perform the described/depicted function. Alternatively or additionally, portions of the invention described/depicted as two or more separate processes or steps may be integrated into a single process or step to perform the described/depicted function.

Variations of embodiments of the present invention that are described and embodiments of the present invention comprising different combinations of features noted in the described embodiments can be combined in all possible combinations including, but not limited to use of features described in the context of one embodiment in the context of any other embodiment. Specifically, features described in the context of a method may be incorporated into an apparatus or system and features described in the context of an apparatus or system may be used in practice of a method. The scope of the invention is limited only by the following claims.

In the description and claims of the present application, each of the verbs "comprise", "include" and "have" as well as any conjugates thereof, are used to indicate that the object or objects of the verb are not necessarily a complete listing of members, components, elements or parts of the subject or subjects of the verb.

All publications and/or patents and/or product descriptions cited in this document are fully incorporated herein by reference to the same extent as if each had been individually incorporated herein by reference.

The invention claimed is:

1. A method of image processing, the method comprising:
    (a) calculating a first pixel color feature (PCF) value for each pixel in a color image to generate a set of PCF data;
    (b) applying two adaptive smoothing filters to said first PCF value, wherein the two adaptive smoothing filters have respective fine and coarse smoothing parameters, thereby determining two new PCF values for said first PCF value at each pixel in said color image;
    (c) differencing between said two new PCF values thereby producing a spatial adaptive bandpass filter (ABPF) for each pixel, whereby said different smoothing parameters define a degree of local contrast with respect to adjacent regions; and
    (d) enhancing and detecting the image regions having said degree of local contrast therebetween.

2. A method of image processing according to claim 1, wherein practice of the method alters color Saturation and substantially preserves Hue of the image.

3. A method according to claim 1, wherein said differencing comprises modifying a color of at least one pixel.

4. A method according to claim 3 wherein the first PCF is solely a function of color components of the image.

5. A method according to claim 3 wherein the first PCF is solely a function of color components of a pixel for which the PCF value is calculated.

6. A method according to claim 3 wherein the first PCF is based on a ratio of at least 2 color components.

7. A method according to claim 3, wherein calculating comprises calculating a visual perception enhancement PCF.

8. A method according to claim 3, wherein calculating comprises calculating a color feature which matches a spectra of a tissue absorbance of interest.

9. A method of image processing according to claim 3 wherein the first PCF includes at least one term indicating a difference between color components.

10. A method of image processing according to claim 9, wherein the difference between color components is a difference between color components of the image.

11. A method of image processing according to claim 3, wherein the first PCF functions as a spectral filter which emphasizes red in the image.

12. A method of image processing according to claim 3, wherein the first PCF functions as a spectral filter which emphasizes blue in the image.

13. A method of image processing according to claim 3, wherein the first PCF includes a normalization component.

14. A method of image processing according to claim 3, wherein the first PCF functions as a spectral filter which evaluates similarity to at least one difference in a hemoglobin absorbance spectra.

15. A method of image processing according to claim 14, wherein the first PCF functions as a spectral filter which evaluates similarity to at least two differences in a hemoglobin absorbance spectra.

16. A method according to claim 1, wherein said differencing comprises maintaining the color of substantially all the pixels in the image.

17. A method according to claim 16, comprising correcting the image after said differencing to maintain a color of said pixels.

18. A method according to claim 16, comprising limiting modification of said image to within saturation of at least one of a representation of said image and a display of said image.

19. A method according to claim 16, comprising separately filtering each color component of said image.

20. A method according to claim 1, wherein said differencing comprises producing a plurality of bandpass filters.

21. A method according to claim 20, comprising combining the results of said filters.

22. A method of image processing according to claim 1, wherein the spatial adaptive bandpass filter defines edges of regions.

23. A method of image processing according to claim 1, wherein said differencing comprises thresholding of spatial adaptive bandpass filter results.

24. A method of image processing according to claim 1, wherein the spatial adaptive bandpass filter defines regions without a priori size criteria.

25. A method of image processing according to claim 1, wherein said differencing emphasizes at least one region of the image to indicate an amount of oxyhemoglobin.

26. A method of image processing according to claim 1, wherein said differencing emphasizes at least one region to indicate an amount of deoxyhemoglobin.

27. A method of image processing according to claim 1, wherein the image is an endoscopic image.

28. A method of image processing according to claim 1, wherein the image is acquired using broadband light.

29. A method of image processing according to claim 1, wherein the image is acquired using narrowband light.

30. A method of image processing according to claim 1, comprising repeating (a) and (b) for at least two levels of sensitivity of differentiation between regions.

31. A method of image processing according to claim 30, comprising repeating (a) and (b) for at least three levels of sensitivity of differentiation between regions.

32. A method of image processing according to claim 1, comprising repeating (a) and (b) for at least two types of filtering results, one corresponding to a visual perception enhancement PCF and one corresponding to a spectral enhancement PCF.

33. A method of image processing according to claim 1, comprising repeating (a) on a result of (b).

34. A method of image processing according to claim 1, comprising applying (a) and (b) as a single combined filter.

35. A method according to claim 1 wherein the first PCF value for at least one pixel depends on at least 2 color components of the image.

36. A method according to claim 1, wherein said calculating further includes calculating n additional first PCF values for each pixel in the color image, wherein n is an integer from 1 to 6;
wherein said applying further includes applying the two adaptive smoothing filters to said n additional first PCF values, thereby determining n additional pairs of new PCF values for the first n additional PCF values at each pixel in the said color image; and
wherein said differencing includes differencing between said n additional pairs of new PCF values, thereby producing n additional spatial ABPFs for each pixel.

37. The method of claim 1, wherein said first PCF value is indicative of Red, Green, and Blue color values for each pixel.

38. The method of claim 1, wherein said color image is a medical image.

39. The method of claim 1, wherein said method has at least one of a medical application and an aesthetic application.

40. The method of claim 1, wherein said method is applied in at least one of screening and tracking of at least one of skin abnormalities and diseases.

41. The method of claim 1, wherein said color image is of one of a cut, acne, disfigurement, cancerous mole, lesion, and blemishes.

42. The method of claim 1, wherein said color image is of one of an external body surface, an internal body tissue, and an internal body organ.

43. The method of claim 1, wherein said color image is produced by a digital camera.

44. The method of claim 1, wherein said color image is acquired by an intrabody camera.

45. The method of claim 44, wherein the intrabody camera is one of an endoscopic camera, a laparoscopic camera, a colonoscopic camera, and a swallowed camera.

46. A method according to claim 1, wherein said enhancing results in said degree of local contrast being visibly discernable.

47. A method according to claim 1, wherein said enhancing includes retaining a natural color scheme.

48. The method of claim 1, wherein said image regions have unknown dimensions.

49. The method of claim 1, wherein said enhancing includes increasing luminance and increasing part of spectra.

50. The method of claim 1, wherein said detecting is based on increased/enhanced color intensity.

51. The method of claim 1, wherein said detecting includes identifying color absorption changes based on increases in parts of spectra.

52. The method according to claim 1, wherein said detecting is one of visual display enhancement via processing for emphasizing, and automated using detection processing via thresholding and overlay.

* * * * *